US011555997B2

(12) United States Patent
Stith et al.

(10) Patent No.: US 11,555,997 B2
(45) Date of Patent: Jan. 17, 2023

(54) ENDOSCOPE WITH INTEGRATED MEASUREMENT OF DISTANCE TO OBJECTS OF INTEREST

(71) Applicant: EndoChoice, Inc., Alpharetta, GA (US)

(72) Inventors: Curtis William Stith, Santa Cruz, CA (US); Edward Andrew Jakl, Scotts Valley, CA (US)

(73) Assignee: EndoChoice, Inc., Alpharetta, GA (US)

( * ) Notice: Subject to any disclaimer, the term of this patent is extended or adjusted under 35 U.S.C. 154(b) by 819 days.

(21) Appl. No.: 16/518,640

(22) Filed: Jul. 22, 2019

(65) Prior Publication Data
US 2019/0346670 A1 Nov. 14, 2019

Related U.S. Application Data

(63) Continuation of application No. 15/137,760, filed on Apr. 25, 2016, now Pat. No. 10,401,611.
(Continued)

(51) Int. Cl.
*A61B 1/00* (2006.01)
*G02B 23/24* (2006.01)
(Continued)

(52) U.S. Cl.
CPC ........ *G02B 23/2423* (2013.01); *A61B 1/0005* (2013.01); *A61B 1/00006* (2013.01);
(Continued)

(58) Field of Classification Search
CPC .............. A61B 1/00006; A61B 1/0005; A61B 1/00057; A61B 1/0011; A61B 1/00188; G02B 23/2423; G02B 7/04; G02B 7/28
See application file for complete search history.

(56) References Cited

U.S. PATENT DOCUMENTS

| 3,639,714 A | 2/1972 | Fujimoto |
| 3,955,064 A | 5/1976 | Demetrio |

(Continued)

FOREIGN PATENT DOCUMENTS

| CA | 2297986 | 3/1999 |
| CA | 2765559 | 12/2010 |

(Continued)

OTHER PUBLICATIONS

Office Action dated Jun. 30, 2016 for U.S. Appl. No. 13/655,120; (3596-141).

(Continued)

*Primary Examiner* — Timothy J Neal
*Assistant Examiner* — William B Chou
(74) *Attorney, Agent, or Firm* — Bookoff McAndrews, PLLC

(57) ABSTRACT

The present specification describes a method for determining the distance of an object from the tip of an endoscope during an endoscopic procedure, wherein at least one lens is configured to converge light from outside the tip onto a sensor that includes a plurality of photodiodes a portion of which are adjacent pairs of photodiodes configured to be phase detection pixels. The method includes receiving light into each adjacent pair of photodiodes, wherein said light is reflected off a surface of said object; determining a first response curve to said light for a first photodiode of said adjacent pair of photodiodes and a second response curve to said light for a second photodiode of said adjacent pair of photodiodes; identifying an intersection between the first response curve and the second response curve; and using data derived from said intersection to determine said distance to the object.

16 Claims, 21 Drawing Sheets

Related U.S. Application Data

(60) Provisional application No. 62/153,316, filed on Apr. 27, 2015.

(51) Int. Cl.
*G02B 7/04* (2021.01)
*G02B 7/28* (2021.01)

(52) U.S. Cl.
CPC ........ *A61B 1/0011* (2013.01); *A61B 1/00057* (2013.01); *A61B 1/00188* (2013.01); *G02B 7/04* (2013.01); *G02B 7/28* (2013.01)

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Ore |
| 4,877,314 A | 10/1989 | Kanamori |
| 4,962,115 A | 2/1990 | Takahashi |
| 4,976,522 A | 12/1990 | Igarashi |
| 4,984,878 A | 1/1991 | Miyano |
| 5,007,466 A | 4/1991 | Takahashi |
| 5,014,885 A | 5/1991 | Akahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,562 A | 5/1996 | Kaplan |
| 5,547,455 A | 8/1996 | McKenna et al. |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna et al. |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | Ebbesmeier |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,346,940 B1 * | 2/2002 | Fukunaga ............... G06T 15/20 382/103 |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,690,337 B1 | 2/2004 | Mayer, III |
| 6,712,760 B2 | 3/2004 | Sano |
| 6,832,984 B2 | 12/2004 | Stelzer |
| 6,873,012 B2 | 3/2005 | Stecher |
| 6,888,119 B2 | 5/2005 | Iizuka |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,715,661 B2 | 5/2010 | Yasui |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,978,462 B2 | 7/2011 | Wright |
| 7,990,461 B2 | 8/2011 | Kinugasa |
| 7,994,465 B1 | 8/2011 | Bamji |
| 8,064,866 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,534 B1 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,742,309 B2 | 6/2014 | Agranov et al. |
| 8,797,392 B2 | 8/2014 | Bayer |
| 8,872,906 B2 | 10/2014 | Bayer |
| 8,928,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |
| 2001/0036322 A1 | 11/2001 | Blomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |

(56) References Cited

U.S. PATENT DOCUMENTS

| | | |
|---|---|---|
| 2003/0063398 A1 | 4/2003 | Abe |
| 2003/0076411 A1 | 4/2003 | Iida et al. |
| 2003/0083552 A1 | 5/2003 | Remijan |
| 2003/0128893 A1 | 7/2003 | Castorina |
| 2003/0139850 A1 | 7/2003 | Homna |
| 2003/0153897 A1 | 8/2003 | Russo |
| 2003/0183029 A1 | 10/2003 | Sonnerschen |
| 2003/0188503 A1 | 10/2003 | Matsumoto |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0180682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020878 A1 | 1/2005 | Shioda |
| 2005/0038317 A1 | 2/2005 | Ratnakar |
| 2005/0047134 A1 | 3/2005 | Mueller |
| 2005/0057687 A1 | 3/2005 | Irani |
| 2005/0090709 A1 | 4/2005 | Okada |
| 2005/0098501 A1 | 5/2005 | Stelzer |
| 2005/0124858 A1 | 6/2005 | Matsuzawa |
| 2005/0110527 A1 | 8/2005 | Banik |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277608 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0091085 A1 | 5/2006 | Oshima |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215488 A1 | 9/2006 | Thrailkill |
| 2006/0246771 A1 | 11/2006 | ONeal |
| 2006/0252994 A1 | 11/2006 | Ratnakar |
| 2006/0264704 A1 | 11/2006 | Fujimori |
| 2006/0293556 A1 | 12/2006 | Gamer |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088183 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0187681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0270642 A1 | 11/2007 | Bayer |
| 2007/0285492 A1 | 11/2007 | Sonnenschein |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0048797 A1 | 2/2008 | Yasushi |
| 2008/0058601 A1 | 3/2008 | Fujimori |
| 2008/0071290 A1 | 3/2008 | Larkin |
| 2008/0130108 A1 | 6/2008 | Bayer |
| 2008/0151070 A1 | 6/2008 | Shiozawa et al. |
| 2008/0161646 A1 | 7/2008 | Gomez |
| 2008/0163652 A1 | 7/2008 | Shatskin |
| 2008/0167520 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spindler |
| 2008/0221388 A1 | 9/2008 | Seibel et al. |
| 2008/0235206 A1 | 9/2008 | Cotter |
| 2008/0253686 A1 | 10/2008 | Bayer |
| 2008/0282312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0225159 A1 | 9/2009 | Schneider |
| 2009/0225217 A1 | 9/2009 | Katsuda |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0136822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0176273 A1 | 7/2010 | Shimoda |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2010/0326703 A1 | 12/2010 | Grlad |
| 2011/0004058 A1 | 1/2011 | Oneda |
| 2011/0004059 A1 | 1/2011 | Arneson |
| 2011/0034769 A1 | 2/2011 | Adair |
| 2011/0063427 A1 | 3/2011 | Fengler |
| 2011/0076001 A1 | 3/2011 | Iwasaki |
| 2011/0084835 A1 | 4/2011 | Whitehouse |
| 2011/0140003 A1 | 6/2011 | Beck |

(56) References Cited

U.S. PATENT DOCUMENTS

| | | |
|---|---|---|
| 2011/0160535 A1 | 6/2011 | Bayer |
| 2011/0180530 A1 | 6/2011 | Ratnakar |
| 2011/0169931 A1 | 7/2011 | Pascal |
| 2011/0184243 A1 | 7/2011 | Wright |
| 2011/0211267 A1 | 9/2011 | Takato |
| 2011/0254937 A1 | 10/2011 | Yoshino |
| 2011/0263938 A1 | 10/2011 | Levy |
| 2011/0273599 A1 | 11/2011 | Murata |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0162402 A1 | 6/2012 | Amano |
| 2012/0193515 A1 | 8/2012 | Agranov |
| 2012/0200683 A1 | 8/2012 | Oshima |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0280858 A1 | 11/2012 | Ouyang |
| 2012/0281536 A1 | 11/2012 | Gell |
| 2012/0300999 A1 | 11/2012 | Bayer |
| 2013/0021508 A1 | 1/2013 | Uranishi |
| 2013/0053646 A1 | 2/2013 | Yamamoto |
| 2013/0057724 A1 | 3/2013 | Miyahara |
| 2013/0060086 A1 | 3/2013 | Talbert |
| 2013/0077257 A1 | 3/2013 | Tsai |
| 2013/0086297 A1 | 3/2013 | Shtul |
| 2013/0085329 A1 | 4/2013 | Morissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0141557 A1 | 6/2013 | Kawata |
| 2013/0150671 A1 | 6/2013 | Levy |
| 2013/0158344 A1 | 6/2013 | Taniguchi |
| 2013/0169843 A1 | 7/2013 | Ono |
| 2013/0172670 A1 | 7/2013 | Levy |
| 2013/0172676 A1 | 7/2013 | Levy |
| 2013/0182156 A1 | 7/2013 | Moriya |
| 2013/0197309 A1 | 8/2013 | Sakata |
| 2013/0197556 A1 | 8/2013 | Shelton |
| 2013/0222640 A1 | 8/2013 | Baek |
| 2013/0235237 A1 | 9/2013 | Aoki |
| 2013/0253268 A1 | 9/2013 | Okada |
| 2013/0258168 A1 | 10/2013 | Aoki |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0197418 A1 | 4/2014 | Ratnakar |
| 2014/0148644 A1 | 5/2014 | Levi |
| 2014/0184766 A1 | 7/2014 | Amling |
| 2014/0213850 A1 | 7/2014 | Levy |
| 2014/0225998 A1 | 8/2014 | Dai |
| 2014/0276207 A1 | 9/2014 | Quyang |
| 2014/0285627 A1 | 9/2014 | Kuboi |
| 2014/0296628 A1 | 10/2014 | Kirma |
| 2014/0296643 A1 | 10/2014 | Levy |
| 2014/0296866 A1 | 10/2014 | Salman |
| 2014/0298932 A1 | 10/2014 | Okamoto |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0215614 A1 | 7/2015 | Witt |
| 2015/0223676 A1 | 8/2015 | Bayer |
| 2015/0230898 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0018873 A1 | 1/2016 | Fernald |
| 2016/0058268 A1 | 3/2016 | Salman |
| 2016/0301855 A1 | 10/2016 | Imade |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1988425 | 9/2008 |
| EP | 1966541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |

(56) References Cited

FOREIGN PATENT DOCUMENTS

| | | |
|---|---|---|
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2008049324 | 4/2009 |
| WO | 2009049322 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2814183012 | 11/2014 |
| WO | 2814210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112899 | 7/2015 |
| WO | 2815134060 | 9/2015 |
| WO | 2015112747 | 11/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Acton dated: Jul. 22, 2016 for U.S. Appl. No. 14/549,265.
Sherman L.M., Plastics That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated: Apr. 28, 2016 for U.S. Appl. No. 13/992,014.
Notice of Allowance dated Aug. 26, 2016 for U.S. Appl. No. 13/212,627.
Office Action dated: Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/007,513.
Office Action dated Dec. 30, 2018 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20,2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 24, 2017 for U.S. Appl. No. 14/838,509.
Notice of Allowance dated Apr. 12, 2017 for U.S. Appl. No. 14/603,137.
Notice of Allowance dated Apr. 18, 2017 for U.S. Appl. No. 13/713,449.
Office Action dated Apr. 19, 2017 for U.S. Appl. No. 14/988,851.
Notice of Allowability dated Apr. 21, 2017 for U.S. Appl. No. 14/548,265.

(56) References Cited

OTHER PUBLICATIONS

Office Action dated May 11, 2017 for U.S. Appl. No. 14/278,293.
Office Acton dated May 10, 2017 for U.S. Appl. No. 14/988,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report fer PCT/US14/37004, dated Sep. 25, 2014.
International Search Report for PCT/US2014/037526, dated Oct. 16, 2814.
International Search Report for PCT/US14/38094, dated Nov. 6, 2014.
International Search Report for PCT/US2015/012751, dated Jun. 26, 2015.
International Search Report for PCTIUS2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action date Feb. 26, 2016 for U.S. Appl. No. 14/274,323.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

\* cited by examiner

Figure 3A
Figure 3B
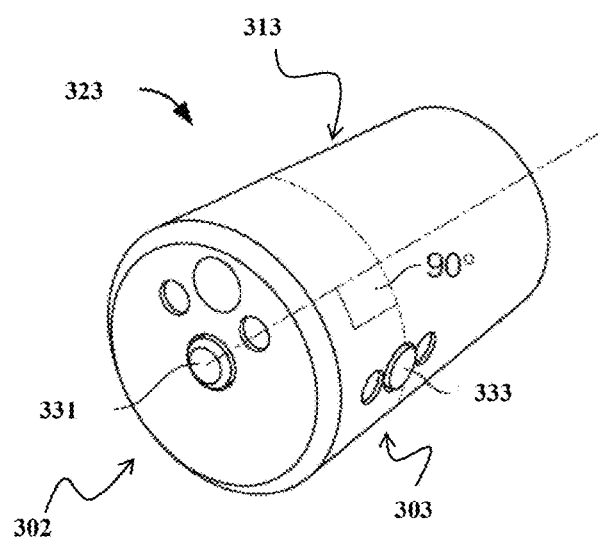
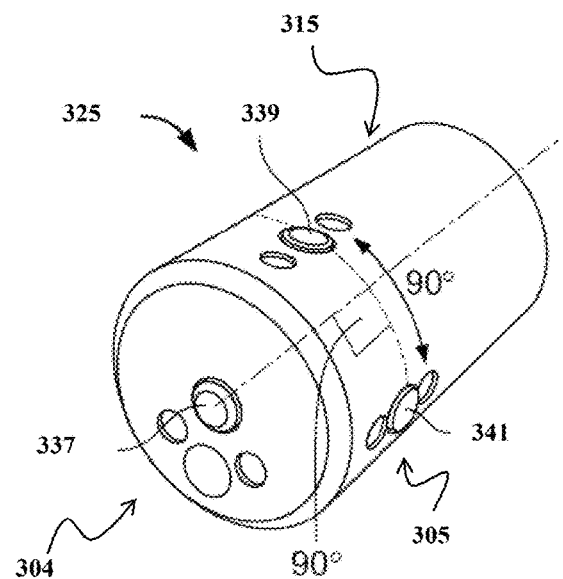

ENDOSCOPE WITH INTEGRATED MEASUREMENT OF DISTANCE TO OBJECTS OF INTEREST

CROSS-REFERENCE

This application is a continuation of U.S. Nonprovisional Patent Application No. 15/137,760, filed on Apr. 25, 2016, which claims the benefit of priority of U.S. Provisional Patent Application No. 62/153,316, filed on Apr. 27, 2015. Each of the above-mentioned applications is herein incorporated by reference in its entirety.

FIELD

The present specification relates generally to endoscopes, and more specifically, to methods and systems for the measurement of the distance of the distal tip of endoscope to objects of interest as it travels through the lumen during endoscopic procedures, and the subsequent determination of the size of those objects.

BACKGROUND

Endoscopes have attained great acceptance within the medical community, since they provide a means for performing procedures, while enabling the physician to view the internal anatomy of the patient. Over the years, numerous endoscopes have been developed and categorized according to specific applications, such as cystoscopy, colonoscopy, laparoscopy, upper GI endoscopy among others. Endoscopes may be inserted into the body's natural orifices or through an incision in the skin.

An endoscope typically comprises an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

When using an endoscope, a common problem is to be able to maneuver the inspection end (distal end) of the scope and position it in proximity to the area of interest. This maneuvering is performed by a trained operator, who uses a combination of the visual inspection of images and tactile coordination to maneuver through the various twists and turns of a patient's GI system. The operator subjectively senses the resistance to maneuvers by the "feel" of the instrument and anticipates the amount of force necessary to advance the endoscope shaft forward. The application of force to the colon and its anatomic attachments can be painful. Particularly undesirable is the frequent occurrence of excessive contact pressure on an internal tissue, which can result in pain and in some cases in perforation.

In particular, the task of inserting the insertion section of the endoscope into the large intestine is a complex one, because the large intestine itself has a complex shape and further, the shape of the large intestine varies from patient to patient. Thus, while inserting and maneuvering the endoscope through the large intestine, precision is required. Also, adjustments are required in the insertion amount (distance travelled by the endoscope through the lumen) and the amount of force used, to achieve proper results in an endoscopic procedure.

Another disadvantage of existing endoscopes is their limited field of view. A limited field of view may not allow a physician to analyze an area under inspection in full detail. This in turn affects the rate of detection of pathological objects that exist in the body cavity in which the endoscope operates. For example, clinical literature shows that the average adenoma miss rate is over 24%. That is, the detection of cancer is missed in more than 24 of every 100 patients. Further, from a medical industry viewpoint, unless a physician is correctly identifying cancer in at least 20% of cancer patients, the average miss rate is considered higher than industry. Therefore, there is a need in the art for endoscopes that allow a broader field of view. One approach to achieving this purpose is described in U.S. Patent Publication No. 20110263938, assigned to the Applicant of the present specification, which describes the use of multiple cameras in a single endoscope and is incorporated herein by reference.

U.S. Pat. No. 8,742,309 entitled "Imagers with depth sensing capabilities" describes an imager that includes depth sensing pixels. The output image signals of each pair of depth sensing pixels depend on the distance from camera lens to object. An image depth signal may be calculated from the difference between the two output image signals of each pixel pair.

There is a need in the art for endoscopes that provide information to the physician about the distance travelled by the endoscope and the exact location of the distal tip inside the patient's lumen. This would not only assist the physician in performing the endoscopic procedure, but also help in quickly marking a spot where an anomaly is found. Additionally, there is need for endoscopes which can provide information about the size of an anomaly, such as a polyp, when found during the procedure, besides being capable of providing guidance to the physician regarding the scope path. There is also a need for methods and systems for ensuring that the length over which an object remains in focus, for a given viewing element, is consistent across the entire lens of that viewing element, so that objects of interest may be viewed clearly and precisely and without anomalies during an endoscopic procedure.

SUMMARY

In some embodiments, the present specification discloses a method for determining a distance of an object from a tip of an endoscope during an endoscopic procedure, wherein said tip comprises a housing having a distal end and a curved side wall and a first viewing element positioned on said distal end, wherein said first viewing element comprises at least one lens and a sensor, wherein the at least one lens is configured to converge light from outside said tip onto said sensor, wherein said sensor comprises a plurality of photodiodes and wherein a portion of said plurality of photodiodes are adjacent pairs of photodiodes configured to be phase detection pixels, said method comprising: receiving light into each adjacent pair of photodiodes, wherein said light is reflected off a surface of said object; determining a first response curve to said light for a first photodiode of said adjacent pair of photodiodes and a second response curve to said light for a second photodiode of said adjacent pair of photodiodes; identifying an intersection between the first response curve and the second response curve; and using data derived from said intersection to determine said distance to the object.

Optionally, at least 98% of said plurality of photodiodes are not phase detection pixels. Optionally, at most 2% of said plurality of photodiodes are phase detection pixels.

Optionally, said sensor is divided into four quadrants and wherein an equal number of phase detection pixels are present in each of said four quadrants.

Optionally, a single microlens is disposed between said at least one lens and each adjacent pair of photodiodes. Optionally, a single color filter is disposed between said single microlens and each adjacent pair of photodiodes.

Optionally, a first photodiode of said adjacent pair of photodiodes comprises a light opaque mask covering a right portion of said first photodiode and a second photodiode of said adjacent pair of photodiodes comprises a light opaque mask covering a left portion of said second photodiode. Optionally, a length of the right portion is equal to a length of the left portion.

Optionally, a first microlens is disposed between said at least one lens and a first photodiode of the adjacent pair of photodiodes and a second microlens, separate from the first microlens, is disposed between said at least one lens and a second photodiode of the adjacent pair of photodiodes.

Optionally, a first color filter is disposed between said first microlens and the first photodiode of the adjacent pair of photodiodes and a second color filter, separate from the first color filter, is disposed between said second microlens and the second photodiode of the adjacent pair of photodiodes.

Optionally, the first photodiode of said adjacent pair of photodiodes comprises a light opaque mask covering a right portion of said first photodiode and the second photodiode of said adjacent pair of photodiodes comprises a light opaque mask covering a left portion of said second photodiode. Optionally, a length of the right portion is equal to a length of the left portion.

Optionally, said data derived from said intersection comprises an angle of incidence of said light and wherein said angle of incidence is equal for each photodiode in a given adjacent pair of photodiodes.

Optionally, said method further comprises using a processor to apply a first gain to light response data from each of the phase detection pixels, wherein the light response data is the data generated from a signal from at least one of the first photodiode and the second photodiode, where the signal is indicative of the amount of light received by that photodiode. Optionally, the processor is used to apply a second gain to light response data from the plurality of photodiodes other than the phase detection pixels wherein the first gain is larger than the second gain.

Optionally, the method further comprises using a processor to remove light response data generated from at least some of the phase detection pixels from an image and to replace said light response data generated from at least some of the phase detection pixels with light response data derived from photodiodes other than the phase detection pixels.

Optionally, said tip further comprises a second viewing element positioned on said curved side wall, wherein said second viewing element comprises at least one second viewing element lens and a second viewing element sensor, wherein the at least one second viewing element lens is configured to converge light from outside said tip onto said second viewing element sensor, wherein said second viewing element sensor comprises a plurality of photodiodes, wherein a portion of said plurality of photodiodes are adjacent pairs of photodiodes configured to be phase detection pixels, and wherein at least 98% of said plurality of photodiodes are not phase detection pixels.

Optionally, said second viewing element sensor is divided into four quadrants and wherein an equal number of phase detection pixels are present in each of said four quadrants.

Optionally, said first viewing element comprises a CCD sensor.

Optionally, said first viewing element comprises a CMOS sensor.

In some embodiments, the present specification discloses a method for determining a distance of an object from a tip of an endoscope during an endoscopic procedure, wherein said tip comprises a housing having a distal end and a curved side wall and a viewing element positioned on said distal end, wherein said viewing element comprises at least one lens and a sensor, wherein the at least one lens is configured to converge light from outside said tip onto said sensor, wherein said sensor comprises a plurality of photodiodes and wherein a portion of said plurality of photodiodes are adjacent pairs of photodiodes configured to be phase detection pixels, said method comprising: receiving light into each adjacent pair of photodiodes, wherein said light is reflected off a surface of said object; determining a first response to said light for a first photodiode of said adjacent pair of photodiodes and a second response to said light for a second photodiode of said adjacent pair of photodiodes; identifying a value indicative of an intersection point between the first response and the second response; and using data derived from said value to determine said distance to the object.

Optionally, at least 98% of said plurality of photodiodes are not phase detection pixels. Optionally, at most 2% of said plurality of photodiodes are phase detection pixels.

In some embodiments, the present specification discloses a method for determining a distance of an object from a tip of an endoscope during an endoscopic procedure, wherein said tip comprises a housing having a distal end and a curved side wall and a first viewing element positioned on said distal end, wherein said viewing element comprises at least one lens and a sensor, wherein the at least one lens is configured to converge light from outside said tip onto said sensor, wherein said sensor comprises a plurality of photodiodes and wherein a portion of said plurality of photodiodes are adjacent pairs of photodiodes configured to be phase detection pixels, said method comprising: receiving light into each adjacent pair of photodiodes, wherein said light is reflected off a surface of said object; determining an intersection point between a first response curve to said light for a first photodiode of said adjacent pair of photodiodes and a second response curve to said light for a second photodiode of said adjacent pair of photodiodes; and using data derived from said intersection point to determine said distance to the object.

In some embodiments, the present specification discloses an endoscope system that is capable of measuring the distance to objects of interest during an endoscopic procedure, and subsequently determining the size of such objects. In one embodiment, the overlapping field of view (FOV) of two or more cameras in a multi-camera endoscope system is used to measure the distance to an object of interest. In another embodiment, a uniquely constructed CMOS or CCD sensor comprising phase detection pixels is used to capture data enabling the measurement of the distance to objects of interest. In one embodiment, the uniquely constructed sensor provides a method for achieving an optimum focus in the lens assembly of the viewing element. In another embodiment, the estimated path of the scope beyond the distal tip is dynamically projected during an endoscopic procedure, based on the angle of movement of the distal tip as controlled by the endoscope handle and the measurement of distance of the tip of the endoscope from the walls of the lumen.

In some embodiments, the present specification also discloses a method for determining the distance and size of an object of interest during an endoscopic procedure, the endoscope used in the procedure comprising a plurality of viewing elements in its tip section, wherein the fields of view of said viewing elements overlap with each other, said method comprising: using said viewing elements with overlapping fields of view to generate stereo images; determining an object of interest in the stereo images; applying parallax and triangulation techniques to said stereo images to calculate distance to objects of interest; and using the calculated distance and known characteristics of said viewing elements to compute size of the object of interest.

Optionally, the endoscope comprises a front-pointing viewing element located in its tip section for generating a front view. Optionally, the endoscope comprises at least one side-pointing viewing element located at or in proximity to a distal end of said tip section for generating at least one side view. Each of said viewing elements may comprise a lens with a field of view in a range of 120 degrees to 220 degrees. The field of view provided by said front-pointing viewing element may cover a front view. The field of view provided by said one or more side-pointing viewing elements may cover front and side views.

Optionally, each of said viewing elements comprises a CCD sensor. Optionally, each of said viewing elements comprises a CMOS sensor.

In some embodiments, the present specification also discloses a method of manufacturing a lens assembly comprising at least one lens and a detector array, the method comprising: distributing a plurality of pairs of phase detection pixels across said detector array; measuring the response of the plurality of pairs of phase detection pixels; determining an optimum distance and position within an x, y, and z axial dimension between the lens and the detector array based on the measured response, the distance enabling a consistent focus across the lens; and fixing a distance and position of the lens relative to the detector array based on said determining of the optimum distance and position.

Optionally, a pair of phase detection pixels comprises a pair of adjacent photodiodes.

Optionally, the responses of two pixels in a pair of phase detection pixels are equal when an object is in focus. Optionally, the focus is inconsistent at the point where the responses of pixels in a pair are not equal.

The optimum distance between the lens and the detector array may be fixed by adjusting the position of the lens.

In some embodiments, the present specification also discloses an endoscope with multiple viewing elements, comprising: at least one viewing element located in the tip section of the endoscope for generating a front view; one or more displays for displaying views generated from the at least one viewing element concurrently and in real-time; an endoscope handle comprising at least one knob for maneuvering the endoscope through the body during a procedure, wherein the rotation of said knob and the angle of movement of the distal tip of the endoscope are directly co-related; and processing means for generating angular movement data from the rotation of said knob and computing an estimated path of the endoscope based on said angular movement data.

Optionally, the estimated path of the endoscope is projected on the generated front and side views.

Optionally, said projection comprises graphic overlay on the real-time views being generated by the endoscope.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3A illustrates an exemplary configuration of the tip section of a multi-viewing element endoscope;

FIG. 3B illustrates another exemplary configuration of the tip section of a multi-viewing element endoscope;

DETAILED DESCRIPTION

In one embodiment, the present specification discloses an endoscope system that is capable of measuring the distance to objects of interest during an endoscopic procedure, and subsequent determination of the size of such objects. In one embodiment, the overlapping field of view (FOV) of two or more viewing elements in a multi-viewing element endoscope system is used to measure distance to an object of interest. In another embodiment, a uniquely constructed CMOS or CCD sensor comprising phase detection pixels is used to capture data enabling the measurement of the distance to objects of interest. In one embodiment, the uniquely constructed sensor provides a method for achieving an optimum focus in the lens assembly of the viewing element. In another embodiment, the estimated path of the scope beyond the distal tip is dynamically projected during an endoscopic procedure, based on the angle of movement of the distal tip as controlled by the endoscope handle and the measurement of distance of the tip of the endoscope from the walls of the lumen.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
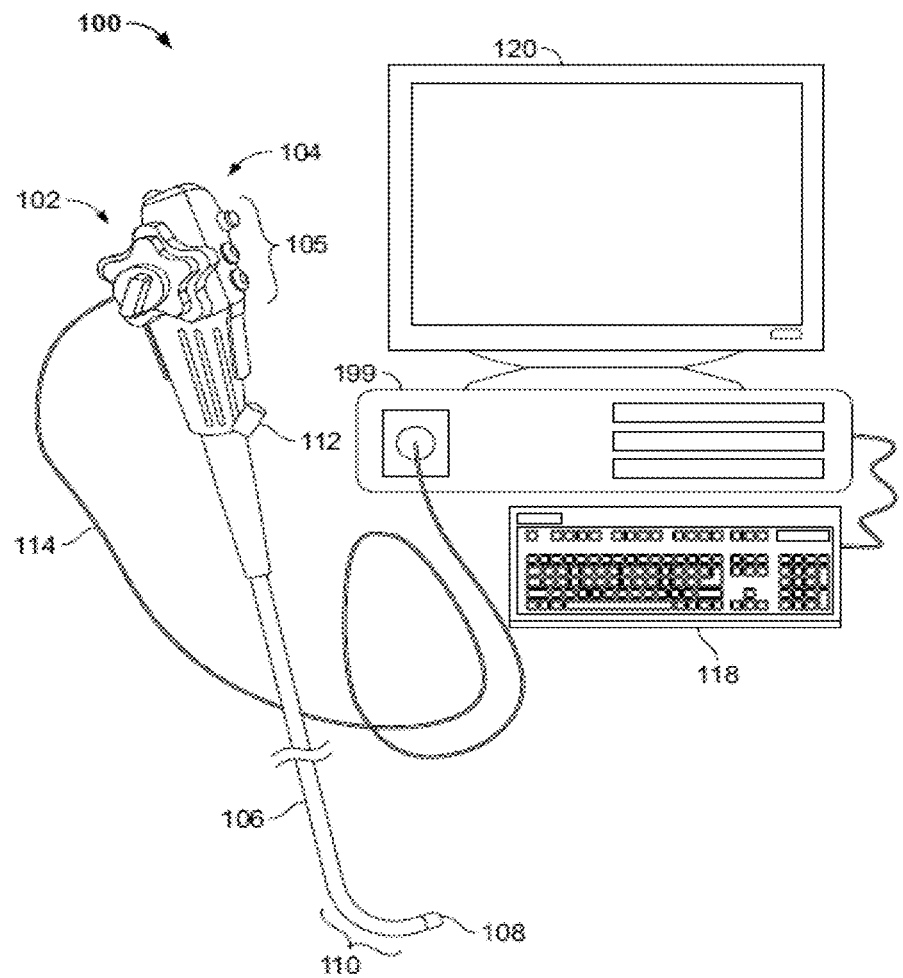
FIG. 1 illustrates an endoscopy system.

Reference is now made to FIG. 1, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. Provisional Patent application Ser. No. 14/263,896, entitled "Video Processing in A Compact Multi-Viewing Element Endoscope System" and filed on Apr. 28, 2014, which is herein incorporated by reference in its entirety.

Figure 2:
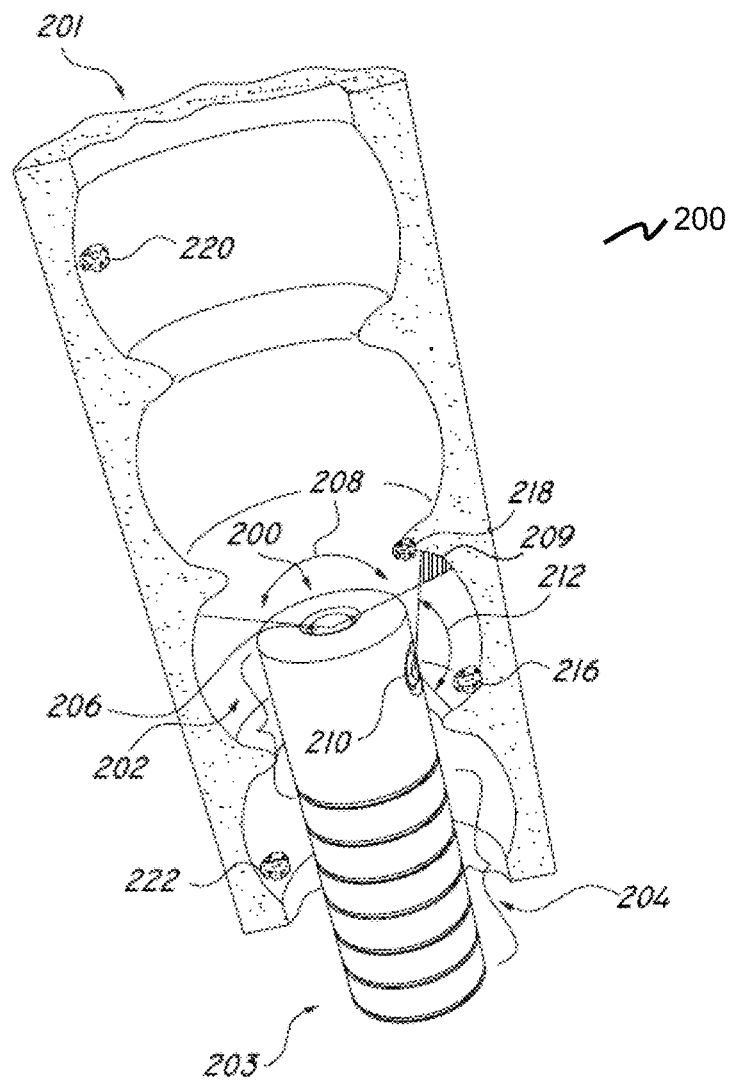
FIG. 2 a cross section of a multi-viewing element endoscope.

Reference is now made to FIG. 2, which shows a cross section of a multi-viewing element endoscope 200, according to an embodiment. Endoscope 200 may include an elongated shaft 203 (not fully shown) terminating with a tip section 202 which is turnable by way of a bending section 204.

Advantageously, tip section may include a front-pointing viewing element 206 as well as a side-pointing viewing element 210. While front-pointing viewing element 206 may be able to detect, based on its field of view 208, polyps such as polyps 218 and 220, side-pointing viewing element 210 may be further able to detect polyps which are normally hidden from the front-pointing viewing element, such as polyp 216. By rotating endoscope 200 around its longitude, side-pointing viewing element 210 may detect polyps circumferentially, 360 degrees around the endoscope. This may enable the detection of polyps such as a polyp 222, which is, similar to polyp 216, located on an inner side of a fold. In other configurations (not shown), two or more side-pointing viewing elements may exist in the tip section, each having a different field of view.

Advantageously, the fields of view of front-pointing viewing element 206 and side-pointing viewing element 210 are at least partially overlapping, such that an object of interest (such as a polyp or another pathology) viewed via the side-pointing viewing element remains in the field of view of this viewing element while the tip section is being turned towards the object, and at least until the object becomes visible through the front-pointing viewing element. This may be beneficial when a polyp is discovered by side-pointing viewing element 210, and the operator desires to perform a surgical operation on that polyp using a surgical tool inserted through a working channel (not shown in the figure) which has an opening in a distal end surface of tip section 202, next to front-pointing viewing element 206. For performing the surgical operation, tip section 202 may need to be turned towards the polyp. Alternately, a side working channel can also be used. It may greatly assist the operator if the fields of view of front-pointing viewing element 206 and side-pointing viewing element 210 have some overlap, so that the polyp remains in sight throughout the turning of the tip section and the operator does not get disoriented.

FIGS. 3A and 3B show two exemplary configurations of the tip section of a multi-viewing element endoscope. In embodiments, the tip section comprises a housing, shown as 313, 315 in FIGS. 3A and 3B, respectively. As shown in FIG. 3A, tip section 323 has a distal end 302 having a front-pointing viewing element 331 positioned thereupon. In addition, tip section 323 has a curved side wall 303 having a side pointing viewing element 333 positioned thereon. In configuration 323, a front-pointing viewing element 331 and a side-pointing viewing element 333 are essentially perpendicular to one another, and have, correspondingly, perpendicular fields of view.

As shown in FIG. 3B, tip section 325 has a distal end 304 having a front-pointing viewing element 337 positioned thereupon. In addition, tip section 323 has a curved side wall 305 having a first side-pointing viewing element 339 and a second side-pointing viewing element 341 positioned thereon. In configuration 325, a front-pointing viewing element 337 is essentially perpendicular to a first side-pointing viewing element 339 and a second side-pointing viewing element 341. First and second side-pointing viewing elements 339, 341 are pointing perpendicularly to one another, and are positioned essentially 90 degrees apart in the cylindrical surface of the tip section. In another configuration (not shown), first and second side-pointing viewing elements may be positioned more than 90 degrees apart in the cylindrical surface of the tip section, such as 120-150 degrees apart or 150-180 degrees apart. For example, the first and second side-pointing viewing elements may be positioned 180 degrees apart, in opposite sides of the cylindrical surface of the tip section, so that they point in opposite directions. In yet further configurations, three or more side-pointing viewing elements may be positioned in the cylindrical surface of the tip section, for example, three viewing elements having 120 degrees in between them. An exemplary endoscopy system is described in co-pending U.S. patent application Ser. No. 14/469,492, entitled "Manifold for a Multiple Viewing Elements Endoscope", and filed on Aug. 26, 2014, which is herein incorporated by reference in its entirety.

Figure 4:
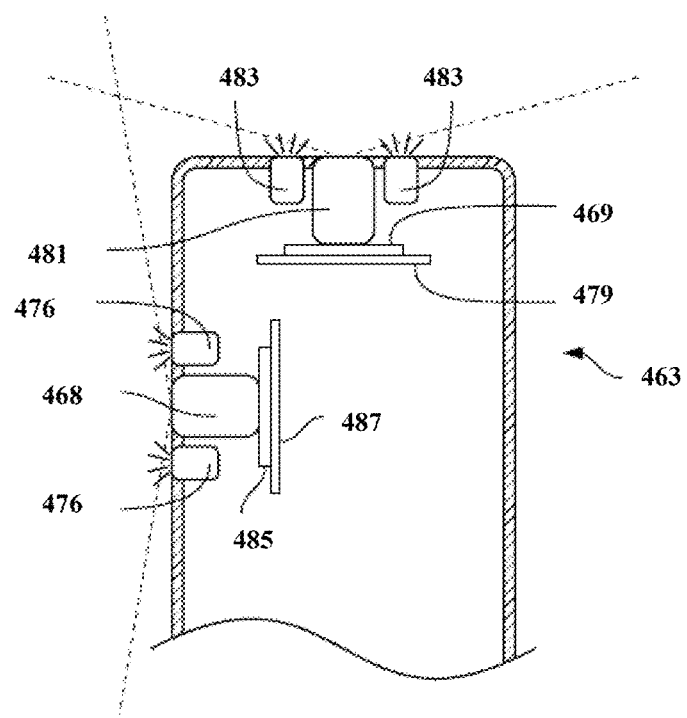
FIG. 4 shows a cross-sectional view of a tip section of a multi-viewing element endoscope.

Reference is now made to FIG. 4, which shows a cross-sectional view of a tip section 463 of a multi-viewing element endoscope, according to an embodiment. Tip section 463 may include a front-pointing image sensor 469, such as a Charge Coupled Device (CCD) or a Complementary Metal Oxide Semiconductor (CMOS) image sensor. Front-pointing image sensor 469 may be mounted on an integrated circuit board 479, which may be rigid or flexible. Integrated circuit board 479 may supply front-pointing image sensor 469 with necessary electrical power and may derive still images and/or video feeds captured by the image sensor. Integrated circuit board 479 may be connected to a set of electrical cables (not shown) which may be threaded through an electrical channel running through the elongated shaft of the endoscope. Front-pointing image sensor 469 may have a lens assembly 481 mounted on top of it and providing the necessary optics for receiving images. Lens assembly 481 may include a plurality of lenses, static or movable, which may provide a field of view of at least 90 degrees and up to essentially 180 degrees. Lens assembly 481 may provide a focal length of about 3 to 100 millimeters. Front-pointing image sensor 469 and lens assembly 481, with or without integrated circuit board 479, may be jointly referred to as a "front pointing viewing element".

The term "focal length" may be used to refer to the distance from a lens to a sensor or may be used to refer to the distance, from the lens, over which an object remains in focus. One of ordinary skill in the art would understand what definition for focal length is being used based on the context and distances discussed.

One or more discrete front illuminators 483 may be placed next to lens assembly 481, for illuminating its field of view. Optionally, discrete front illuminators 483 may be attached to the same integrated circuit board 479 on which front-pointing image sensor 469 is mounted (this configuration is not shown).

Tip section 463 may include a side-pointing image sensor 485, such as a Charge Coupled Device (CCD) or a Complementary Metal Oxide Semiconductor (CMOS) image sensor. Side-pointing image sensor 485 may be mounted on an integrated circuit board 487, which may be rigid or flexible. Integrated circuit board 487 may supply side-pointing image sensor 485 with necessary electrical power and may derive still images and/or video feeds captured by the image sensor. Integrated circuit board 487 may be connected to a set of electrical cables (not shown) which may be threaded through an electrical channel running through the elongated shaft of the endoscope.

Side-pointing image sensor 485 may have a lens assembly 468 mounted on top of it and providing the necessary optics for receiving images. Lens assembly 468 may include a plurality of lenses, static or movable, which may provide a field of view of at least 90 degrees and up to essentially 180 degrees. Lens assembly 468 may provide a focal length of about 2 to 33 millimeters. Side-pointing image sensor 485 and lens assembly 468, with or without integrated circuit board 487, may be jointly referred to as a "side pointing viewing element".

One or more discrete side illuminators 476 may be placed next to lens assembly 468, for illuminating its field of view. Optionally, discrete side illuminators 476 may be attached to the same integrated circuit board 487 on which side-pointing image sensor 485 is mounted (this configuration is not shown).

In another configuration (not shown), integrated circuit boards 479 and 487 may be a single integrated circuit board on which both front and side-pointing image sensors 469 and 485, respectively, are mounted.

Front and side-pointing image sensors 469 and 485 may be similar or identical in terms of, for example, field of view, resolution, light sensitivity, pixel size, focal length, focal distance and/or the like.

Optionally, side-pointing image sensor 485 and lens assembly 468 are advantageously positioned relatively close to the distal end surface of tip section 463. For example, a center of the side-pointing viewing element (which is the center axis of side-pointing image sensor 485 and lens assembly 468) is positioned approximately 7 to 11 millimeters from the distal end of the tip section. This is enabled by an advantageous miniaturizing of the front and side-pointing viewing elements, which allows for enough internal space in the tip section for angular positioning of the viewing elements without colliding.

In one embodiment, the front and side facing viewing elements in a multi-viewing element endoscope are utilized to capture data enabling the measurement of the distance to objects of interest and the determination of their size, while simultaneously capturing the same image for display. This provides the physician with an in situ polyp size estimate during an endoscopic procedure.

Figure 5:
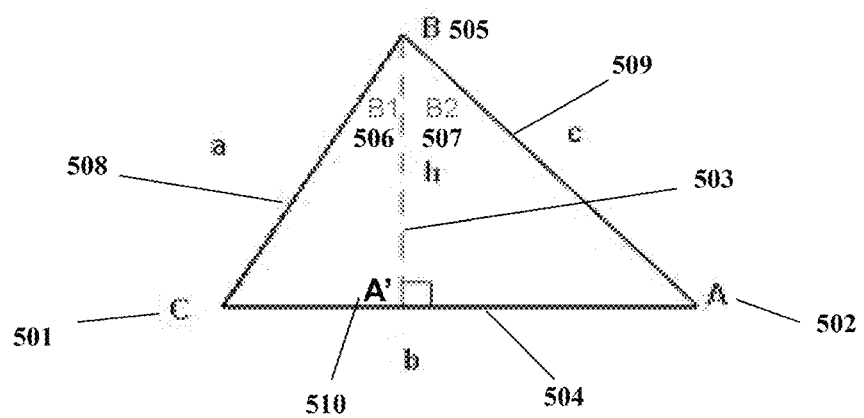
FIG. 5 illustrates the principle of triangulation, which is used for measurement of distance to a point of interest using two image sensors.

FIG. 5 illustrates the principle of triangulation, which is used for measurement of distance to a point of interest using two cameras or image sensors. Referring to FIG. 5, if the positions of the points at Angle C 501 and Angle A 502 are known and Angle C 501 and Angle A 502 can be measured, then one can determine the distance h 503. Further, length CA 504 is known, since it is the distance between the measurement points. Thus:

Angle B 505 is known, since Angle B=180–(Angle A+Angle C)

Angle A' 510 is known, as it is a right triangle.

The sub-angles at B1 506 and B2 507 are known:

B1=180–(90+Angle C)

B2=180–(90+Angle A)

The lengths of side "a" 508, side "c" 509, and "h" 503 can be solved with the Law of Sines, which is known to persons of ordinary skill in the art. For example:

$$h/(\sin C) = a/(\sin A')$$

Figure 6A:
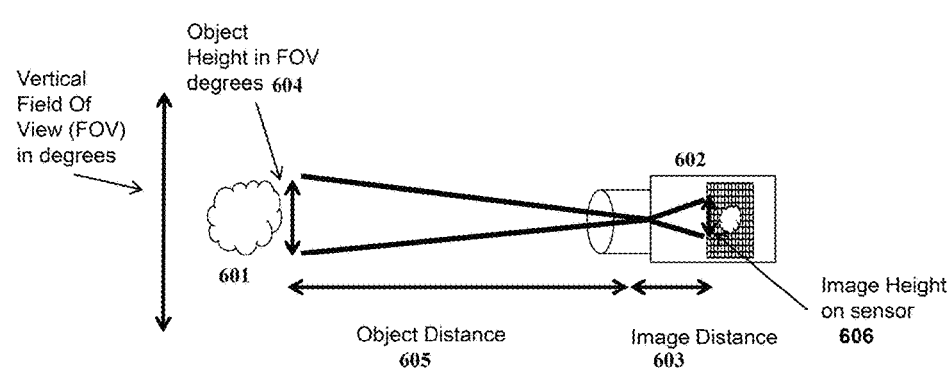
FIG. 6A illustrates how a size of an object can be determined using distance and known camera and sensor characteristics.
Figure 6B:
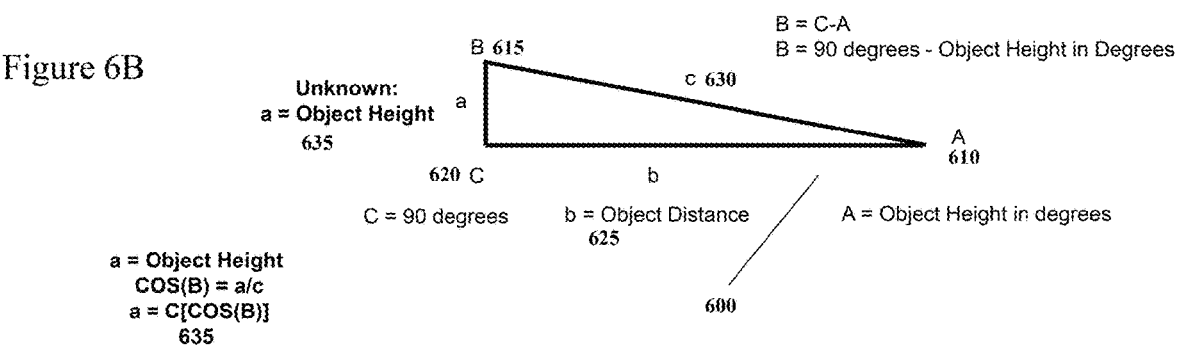
FIG. 6B illustrates size measurement using the method of triangulation.

FIGS. 6A and 6B illustrate how the size of an object can be determined using distance, and known camera and sensor characteristics. The distance is known by the above triangulation method using stereo camera techniques. Referring to FIG. 6A, an object 601 is imaged using a camera 602. Then, with known camera and sensor characteristics, image distance 603, image height on sensor 606 and object height in field of view degrees 604 are known. Now, if the object distance 605 is known, then the actual object height 635 can be computed using triangulations, as shown in FIG. 6B.

Referring to FIG. 6B, the arrangement of FIG. 6A may be mapped to a right angled triangle 600. Here angle A 610 represents object height in degrees, and angle C 620 is equal to 90 degrees. Therefore angle B 615 may be computed as follows:

B=180–(90 degrees+Angle A)

With object distance "b" 625 being known, the height "a" 635 can be computed using the law of Sines:

$$a/(\sin A) = b/(\sin B)$$

The above is a common triangulation method used in stereo camera systems. Typically cameras for stereo imaging are placed side-by-side and these systems work like human eyes.

In multi-viewing element endoscopes, however, imagers are typically placed such that they face 90 degrees away from each other. In one embodiment of the present case, viewing elements are equipped with wide Field of View lens, thereby providing overlap. The overlapping field of view (FOV) of two or more viewing elements in a multi-viewing element endoscope system is then used to measure distance to an object of interest.

In one embodiment, by using the triangulation method with two imagers as explained above, the distance to an object can be determined. Once the distance is known, the object size can be calculated based on the magnification of the lenses of the viewing elements, which is known. The magnification of the lens of a viewing element also depends on the location of the object on the lens. Using the magnification of the lens, the distance from the lens and how many pixels the object covers, the size of the object can be calculated.

Figure 7:
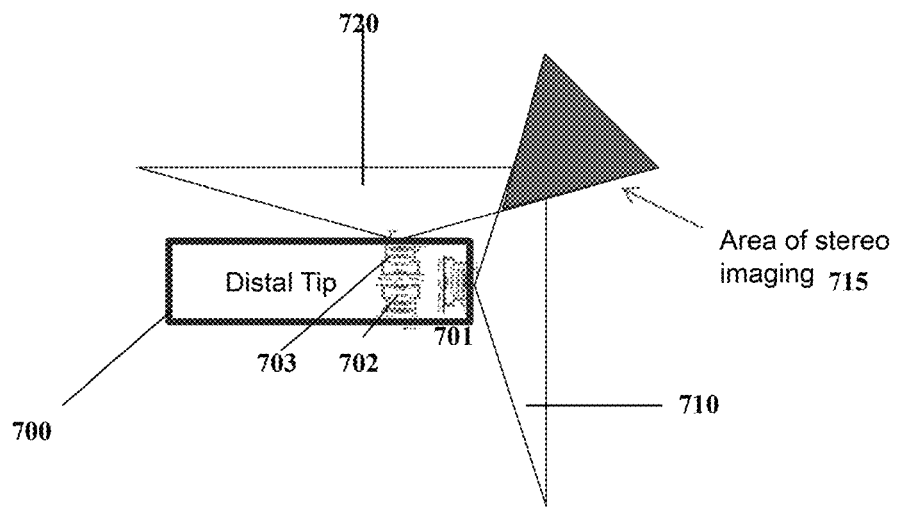
FIG. 7 is an exemplary illustration of the overlapping FOV for an endoscope with two viewing elements, according to one embodiment.

FIG. 7 is an exemplary illustration of the overlapping FOV for an endoscope with two viewing elements. Referring to FIG. 7, distal tip 700 of a multi-viewing element endoscope has a front-pointing viewing element 701 and two side-pointing viewing elements 702 and 703. The fields of view (FOV) of the front viewing element 710 and one of the side viewing elements 720 are seen overlapping in the figure. The region of overlap 715 corresponds to the region of stereo imaging, where a distance measurement may be obtained.

Figure 8:
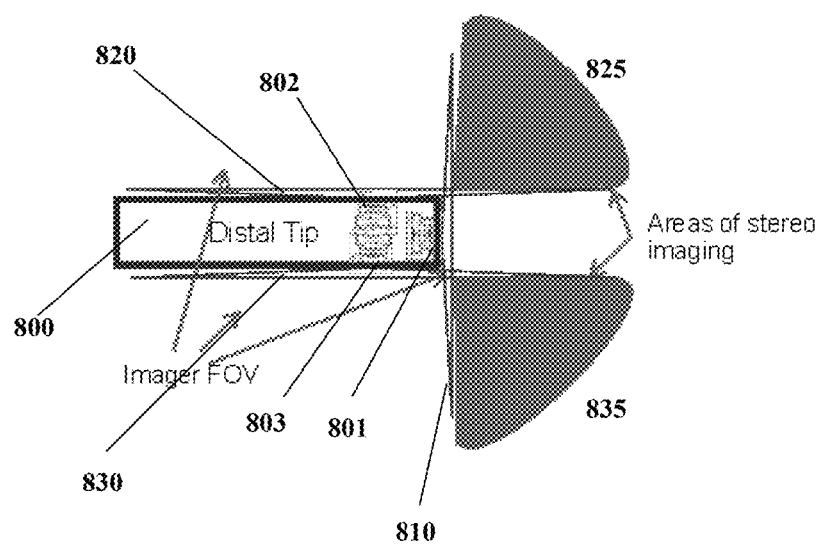
FIG. 8 is an exemplary illustration of the maximum overlapping FOV obtainable when wider FOV lenses are used, according to one embodiment.

FIG. 8 is an exemplary illustration of the maximum overlapping FOV obtainable when wider FOV lenses are used with the placement of viewing elements being same as that shown in FIG. 7. Referring to FIG. 8, distal tip 800 of a multi-viewing element endoscope has a front-pointing viewing element 801 and two side-pointing viewing elements 802 and 803. The field of view (FOV) 810 of the front viewing element overlaps with FOV 820 of the side viewing element 802 to form a first region 825 for stereo imaging. Similarly, the field of view (FOV) 810 of the front viewing element overlaps with FOV 830 of the side viewing element 803 to form a second region 835 for stereo imaging. It may be appreciated that the FOV and corresponding area for distance measurement may be further expanded with adjustments in the placement of viewing elements. The overlapping field of view can be increased by optimizing the placement of viewing elements in the distal tip and/or by increasing the field of view (FOV) of the lenses, for example to 180 degrees.

In one embodiment, the accuracy of the method is further improved by increasing the resolution of the image sensor. This is because in a given system the field of view is divided by the number of pixels of an image sensor. Thus, for a system with 100 degree FOV, and 1000 horizontal pixels, each pixel represents 0.1 degrees. If the resolution increases to 2000 pixels then each pixel represents 0.05 degrees. At a given distance that angle represents a certain area, which is directly proportional. Therefore, if the resolution is increased, the accuracy of the measurement also increases by the same amount. In one embodiment, higher resolution sensors, such as 1-megapixel sensors, are used to increase accuracy by having more pixels per degree of FOV.

As mentioned above, viewing elements may be arranged as one front-facing and one or more side facing. In one embodiment, viewing elements are arranged with two or more front facing. A viewing element may use a CMOS or CCD sensor. Further, the sensor may be equal to or greater than 250×250 in resolution.

Figure 9:
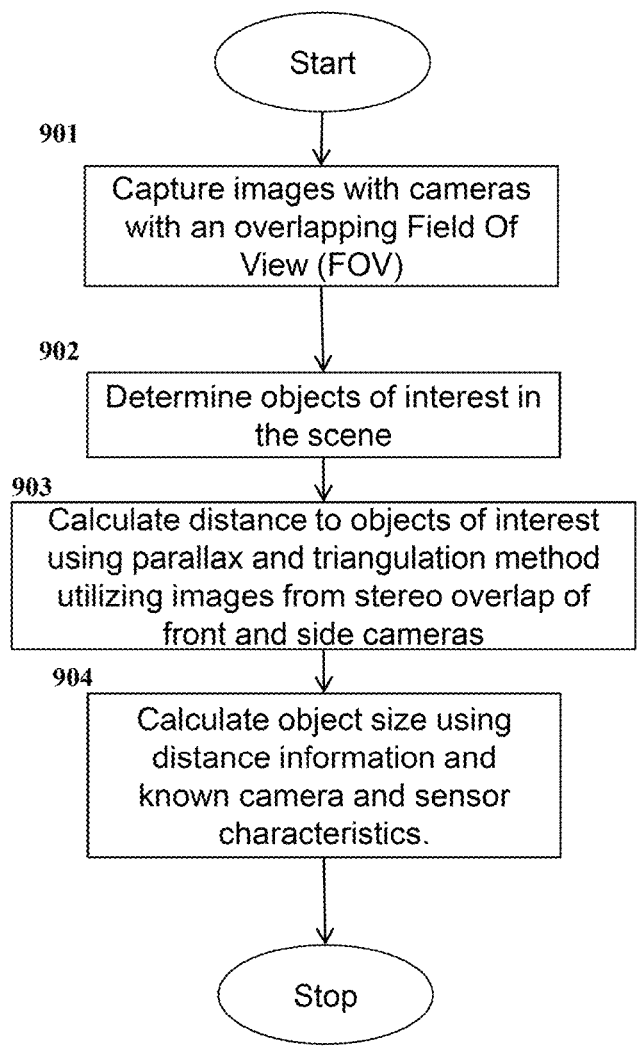
FIG. 9 is a flowchart illustrating the method of computing the distance and size of objects of interest, according to one embodiment of the present specification.

FIG. 9 is a flowchart illustrating the method of computing the distance and size of objects of interest, according to one embodiment of the present specification. This method is achieved by means of a series of programmatic instructions in the main control unit of a multi-viewing elements endoscope. Referring to FIG. 9, in the first step 901, viewing elements with an overlapping field of view (FOV) of a multi-viewing elements endoscope are used to capture images. In the next step 902, objects of interest in the scene are determined either by being marked by the physician or automatically determined by comparing the object characteristics, such as pixel size, shape, color, or texture, to a plurality of known template images and, where a match is found, identifying the object as being one of interest. In the next step 903, the distance to an object of interest is calculated using parallax and triangulation methods and utilizing images from stereo overlap of front and side viewing elements. Finally, object size is calculated using distance information and known characteristics of the sensor and the viewing element, as shown in 904.

In another embodiment, a uniquely constructed CMOS or CCD sensor is used to capture data enabling the measurement of the distance to objects of interest and subsequent determination of their size. In one embodiment, unique pixel construction enables a single sensor to capture distance information while simultaneously generating an image for display during an endoscopic procedure.

Figure 10A:
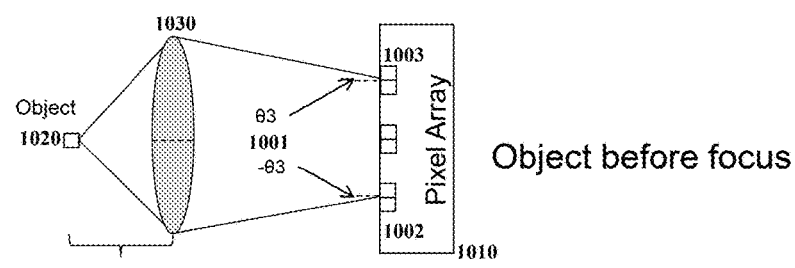
FIG. 10A illustrates the concept of imaging using pixel pairs, according to one embodiment.
Figure 10B:
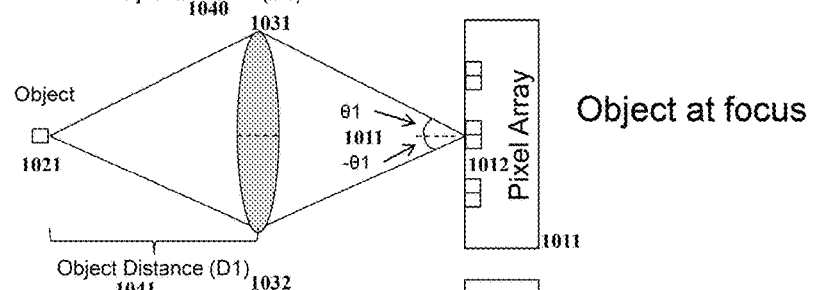
FIG. 10B illustrates the concept of imaging using pixel pairs.
Figure 10C:
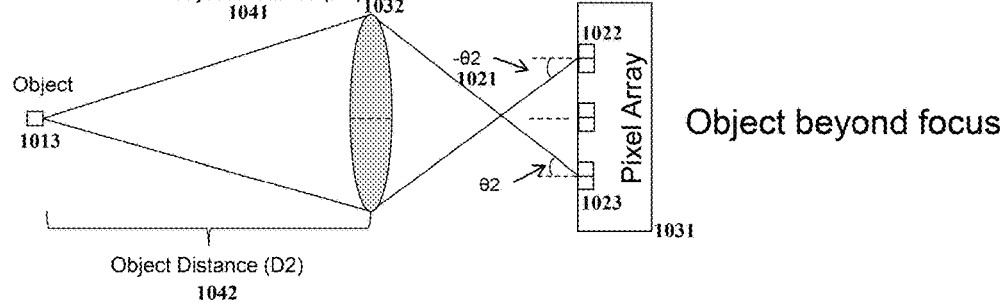
FIG. 10C illustrates the concept of imaging using pixel pairs, according to one embodiment.

FIGS. 10A, 10B and 10C illustrate the concept of imaging using pixel pairs, also known as phase detection pixels. In one embodiment, each pixel pair is defined by two adjacent photodiodes. Referring to FIG. 10A, when the angle 1001 of incident light falling from lens 1030 on pixel pairs 1002 and 1003 of the pixel array 1010 is θ3, the object 1020 is before focus. In this case the distance 1040 of the object from the lens is D3.

Referring to FIG. 10B, when the angle 1011 of incident light falling from lens 1031 on pixel pair 1012 of the pixel array 1011 is θ1, the object 1021 is at focus. In this case, the distance 1041 of the object from the lens is D1.

Referring to FIG. 10C, when the angle 1021 of incident light falling from lens 1032 on pixel pairs 1022 and 1023 of the pixel array 1031 is θ2, the object 1013 is beyond focus. In this case the distance 1042 of the object from the lens is D2.

Figure 11A:
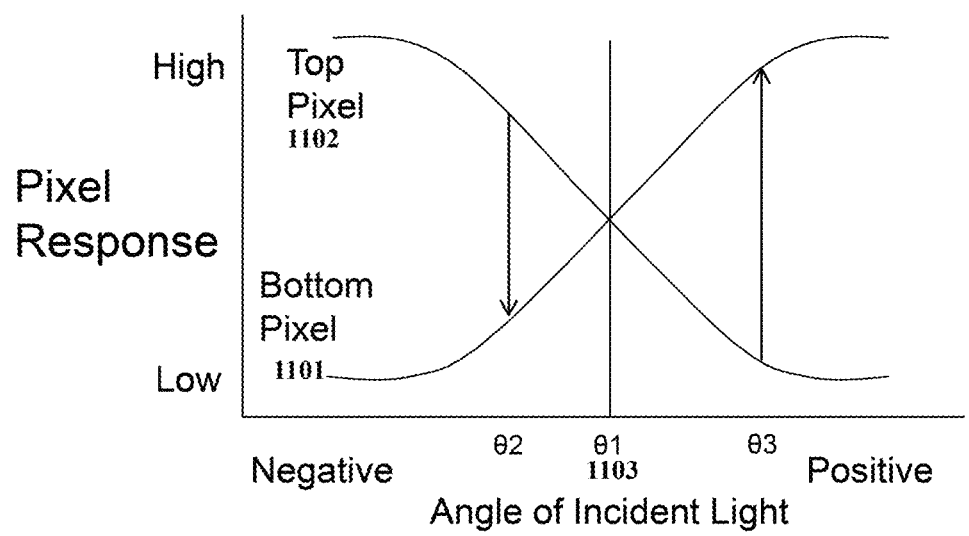
FIG. 11A illustrates the relative response of pixel pairs to angles of incident light.
Figure 11B:
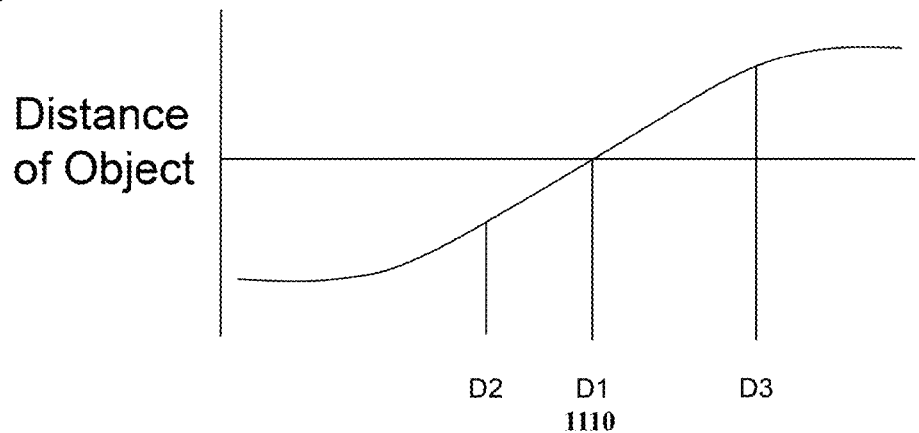
FIG. 11B illustrates the relationship between relative response of pixel pairs and object distance.

FIGS. 11A and 11B illustrate the relationship between relative response of pixel pairs and object distance. Referring to FIG. 11A, it can be seen that the two photodiodes in each pixel pair have symmetrical, but opposing responses to light. Further, the response of the bottom pixel 1101 intersects with the response of the top pixel 1102 at angle θ1 1103 of incident light. Thus, when the angles of incidence into a single pixel pair (as shown in FIG. 10B) are equal, their responses are equal. Because of these responses, it can be determined when an object is in focus, which corresponds to the intersection point 1103 in FIG. 11A. Thus, if the focal length of the lens is known, then the distance to the object in focus can be determined.

Referring to FIG. 11B, it can be seen that distance D1 1110 corresponds to the point where responses of pixels in a pixel pair intersect. Thus, object distance may be determined using relative response of pixel pairs.

It is known in the art that a CMOS or CCD sensor includes an array of pixels. In one embodiment, two adjacent pixels on said sensor form a stereo pixel pair and are used as the base element of a distance measurement system.

Figure 12:
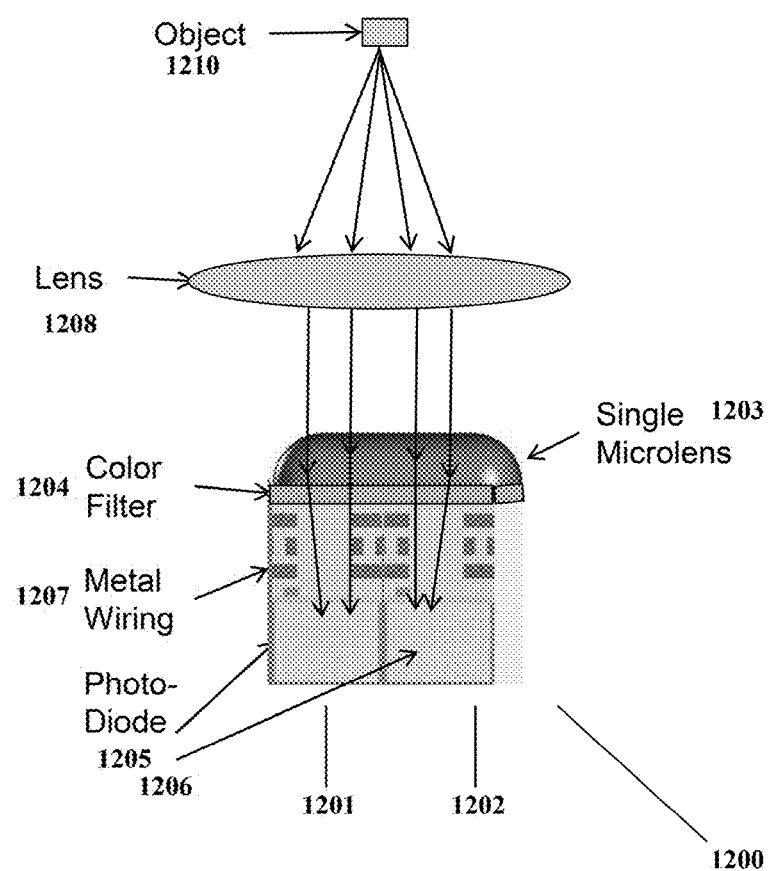
FIG. 12 illustrates a CMOS or CCD sensor including a stereo pixel pair, according to one embodiment.

FIG. 12 illustrates a CMOS or CCD stereo pixel pair, which represents just two of hundreds of thousands of pixels in the sensor, according to one embodiment. Referring to FIG. 12, adjacent pixels 1201 and 1202 form a stereo pixel pair, also referred to as phase detection pixels. The pixel pair may be arranged vertically or horizontally on the sensor array. A single microlens 1203 covers both pixels in the stereo pixel pair. In one embodiment, microlens 1203 is approximately twice the vertical length of a single pixel microlens and approximately the same width as a single pixel microlens.

It may be noted that the number of stereo pixel pairs in an image sensor may be one or more. For more than one pair, in one embodiment a pattern of pixel pairs is located throughout the pixels on the image sensor array. Pixel pairs may be arranged randomly, in a grid or in a repeating pattern, or in any other suitable pattern. In all such cases, however, the stereo pixel pairs represent a tiny minority, preferably less than 2%, 1%, 0.1%, 0.01%, or any increment therein, of all pixels in the sensor.

Beneath the microlens 1203 is a color filter 1204. It is known that CMOS and CCD image sensors are typically processed in silicon, which is sensitive to all visible wavelengths of light. Therefore, in a natural state an image sensor would only be able to discern black, white and grey colors. This requires the use of a color filter. It may be noted that the color filters most often used are for primary colors, namely red, green and blue. This restricts red photons to only the red pixels, blue photons to the blue pixels and green photons to green pixels. Image processing is then used to take the individual color pixel information and recreate a color image. In one embodiment, both pixels 1201 and 1202 in the stereo pixel pair have the same color of color filter array (CFA) material which may be red, green, blue, clear or another color.

In various embodiments, the CFA of various pixel pairs may be different and in any combination of percentages in order to detect the distance of objects of varying colors. For example, 50% of the pixel pairs may have a red CFA, 25% may have a green CFA and 25% may have a blue CFA.

The photo-sensitive part of each pixel is formed by photo diodes 1205, 1206. In one embodiment, each pixel also includes electronics to reset and select the pixel, as well as gain and occasionally other functions or features. Due to other electronics within the pixel, the photosensitive part of a pixel can be less than 50% of the pixel area. The use of microlens 1202 is intended to increase capture of photons by the pixel. For this purpose, the microlens is centered above the photosensitive part of the pixel. Metal wiring 1207 is used to enable the transistor logic and/or provide shielding for the phase detection pixels.

Operationally, incident light from the object 1210 is directed by means of a lens 1208 towards the stereo pixel pair 1201, 1202. Photons that would have otherwise landed on non-photosensitive parts of the pixel are re-directed by the microlens 1203 to the photosensitive areas 1205, 1206. By measuring the difference in the light level of the two pixels in the pixel pair, the angle of incidence of light is discerned. That is, the incident angle is determined by measuring the difference in response of the two pixels, as discussed above. Then, using the angle information from more than one pixel pair the distance of the object can be determined.

Figure 13:
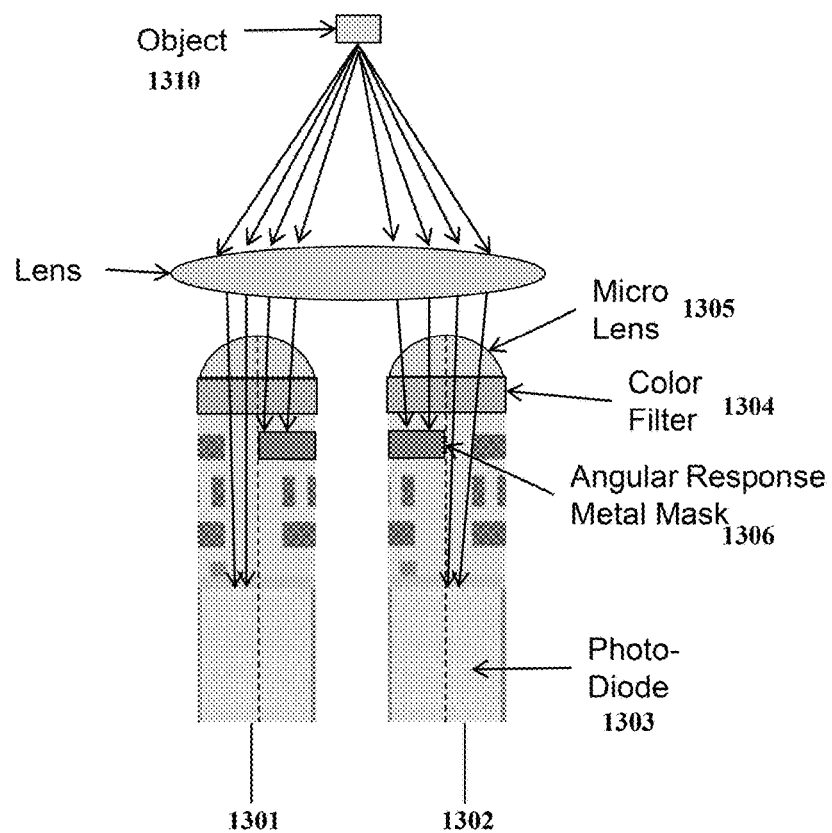
FIG. 13 shows a pair of pixels with individual micro-lenses, according to one embodiment of the present specification.

In another embodiment the pixel pairs are not covered by a single microlens. This embodiment is illustrated in FIG. 13. Referring to FIG. 13, the stereo pixel setup comprises two adjacent pixels 1301 and 1302, which are separated by a known distance. Each pixel comprises a photodiode 1303, a color filter 1304 and a microlens 1305. Further, each pixel also comprises an angular response metal mask 1306, which serves to mask the photodiode. In one embodiment, each pixel in the pair has the photodiode masked in a different position. The two pixels in the pixel pair are complimentary in that each has the opposite side masked. The mask restricts the angles from which light is collected and therefore the amount of light which is collected. Thus for example, if one pixel has the left side of the photodiode masked, the other pixel would have the right side of the photodiode masked. This enables the pixel pair to receive light from substantially different angles and, accordingly, determine the incident angle of the object 1310.

Referring to FIG. 11A, this graph shows the pixel response for a complimentary pixel pair. Pixel response, which may also be termed as light response, may be data corresponding to a signal generated from a photodiode of a pixel, where the data/signal is indicative of the amount of light received by that photodiode. Given known lens characteristics, the angle of incident light may be correlated with the pixel pair response. In FIG. 11B, the relative responses are correlated to the distance of the object observed by the pixel pair.

Pixel masks 1306 may be manufactured in metal, using one of the existing metal layers in the sensor. In alternative embodiments, pixel masks 1306 may be manufactured with any other material that is opaque to the visible light spectrum and may be applied to surface of pixels 1301 and 1302. Multiple pixel pairs across the sensory array allow phase measurements at multiple points across an observed scene, since there is a correlation between the amount of energy (photons) collected and the incident angle, or phase.

In one embodiment, the color of each pixel pair may be matched using the color filter 1304. Light rays captured from a target object or scene may emerge at various angles through mask 1306 to reach photodiode 1303. Photodiode 1303 enables the process of converting received light to current and thus capturing the image or scene on a display.

It may be appreciated that the above methods allow object distances to be measured at multiple points across the scene enabling distance measurement of one or more objects of interest.

Figure 14:
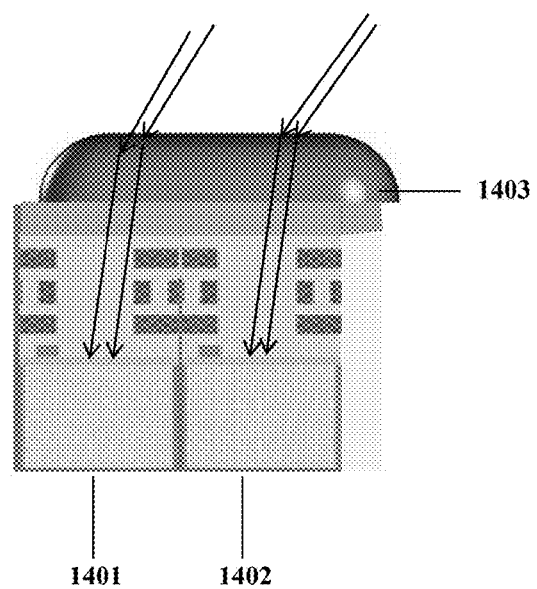
FIG. 14 shows a pixel pair with shifted micro-lens, according to one embodiment.

In one embodiment, a shift of the microlens for one or more pixel pairs is done. Shifted microlens is used to match the chief ray angle (CRA) of the lens and improve the light collection performance. Microlenses which are away from the center of the sensor are shifted, preferably in relation to their distance from the sensor center. This is shown in FIG. 14, where microlens 1403 is placed in a slightly shifted manner over the pixel pair 1401, 1402. In one embodiment, the amount of shift is based on the chief ray angle (CRA) of the camera lens and the relative position of the pixel pair on the sensor such that the shift provides for optimum light collection.

Figure 15:
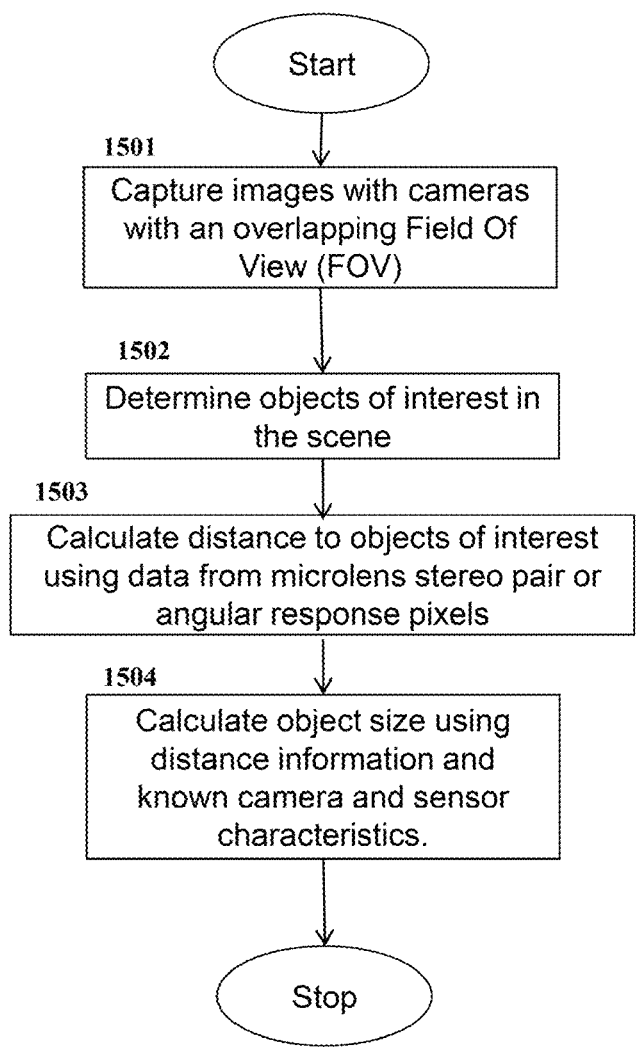
FIG. 15 is a flowchart illustrating the method of computing the distance and size of objects of interest using pixel pairs, according to one embodiment of the present specification.

FIG. 15 is a flowchart illustrating the method of computing the distance and size of objects of interest using pixel pairs, according to one embodiment of the present specification. This method is carried out by means of a series of programmatic instructions in the main control unit of a multi-viewing elements endoscope. Referring to FIG. 15, in the first step 1501, viewing elements with an overlapping field of view (FOV) of a multi-viewing elements endoscope are used to capture images. Preferably, one viewing element is positioned on the front, distal surface of the endoscope tip, a first side viewing element is positioned on the side of the endoscope tip, and a second side viewing element is positioned on the other side of the endoscope tip, opposing the first side viewing element. Additional configurations may be implemented, including one front and one side viewing element, or embodiments with additional viewing elements around the side circumference of the endoscope tip, i.e. 4 side viewing elements positioned equidistant from each other around the endoscope tip periphery.

In the next step 1502, objects of interest in the scene are determined either manually by a physician or automatically as previously explained. A distance to the object of interest is then calculated 1503 using data from the stereo pixel pair with a single microlens or from pixels with angular response masks. Finally, object size is calculated using distance information and known characteristics of the sensor and the viewing element, as shown in 1504.

In one embodiment, the existence of pixel pairs is removed from the displayed image using image processing techniques, thereby enabling the display of the captured image without artifacts from the stereo pixel pairs. Specifically, the phase detection pixel pairs will collect significantly fewer photons than their non-pixel pair neighbors. In one embodiment, fewer photons are collected as each pixel also includes electronics to reset and select the pixel, as well as gain, and occasionally other functions or features. Due to other electronics within the pixel, the photosensitive part of a pixel can be less than 50% of the pixel area. Accordingly, they will therefore appear darker. Using image processing, an automatic gain can be applied to the output of these phase detection pairs to increase their brightness or the pixel pair image may be removed and replaced with an interpolation of neighboring pixels to correct for the removed pixel pair image. Gain applied to the light response data from the phase detection pixel pairs, also referred to as a first gain, may be greater than the gain applied to the rest of the photodiodes (if any is applied at all) in order to account for the greater amount of darkness experienced by the phase detection pixels. Thus, in an embodiment, a second gain is applied to light response data from the plurality of photodiodes other than the phase detection pixels where the first gain may be larger than the second gain.

In one embodiment, the response of pixel pairs to incident light (as explained above with reference to FIGS. 10A-C and 11A-B) is used not only for finding distance to an object, but also for ensuring that the distance over which an object remains in focus, also referred to as the depth of field, is the same across the entire lens. In one embodiment, each of the viewing elements in the present multi-viewing element endoscope system has a fixed the distance over which an object remains in focus across the entire lens. In order to ensure that such a distance is consistent across the entire lens, currently different points in the lens are tested manually. This generally involves viewing different images and visually confirming that the distance over which an object remains in focus is consistent. In one embodiment, the techniques of present specification are used to automate the process of ensuring that the distance over which an object remains in focus is consistent.

Various embodiments of the present specification utilize components in the optical assembly that may be configured to achieve an optimal focus at the time of manufacturing and assembling them. In embodiments, one or more pairs of pixels are utilized to achieve an optimal focus at the detector array, during manufacturing of the lens assembly, disclosed in context of the above description provide with reference to FIGS. 10A-C and 11A-B.

Traditionally, phase detection pixels have been used to enable passive autofocus in cameras where the lens includes a movable element which is moved to bring the image into focus. That is, the lenses are automatically re-positioned in response to phase detection by the pixels. This enables the camera to automatically focus on objects at different distances. This is a common type of autofocus method used in Single Lens Reflex (SLR) cameras. Digital analysis, such as cross-correlation techniques are used to estimate the amount by which the lens should be shifted to the correct position that allows an object to appear 'in-focus'.

In embodiments of the present specification, the optical assembly includes fixed-focus lenses, as mentioned above. As a result, the positions of the lenses are fixed at the time of operation of the viewing element. Medical devices, such as endoscopes, need to be light in weight and spare little space to incorporate additional components. Therefore, any additional components, such as phase detection pixels and equipment to allow shifting of lenses during autofocus may result in an increase in size of a distal tip of the endoscope, rendering it impractical. As a result, fixed-focus lenses are used.

Therefore, in one embodiment phase detection pixels (as shown in FIGS. 12 and 13) are used at the time of manufacturing the lens assembly, to aid in achieving an optimal focus for the detector array. At the time of manufacturing, one or more lenses of the endoscope's viewing element may be positioned to where the phase detection pixels indicate that an optimized focus has been achieved. In embodiments, an optimal focus is achieved when the lenses and a detector array or sensor are placed at an optimal distance in order to generate a clear image or scene of a target object. Digital analysis techniques, such as cross correlation, may be used to aid in determining an optimum distance between the lenses and the detector array.

Figure 16:
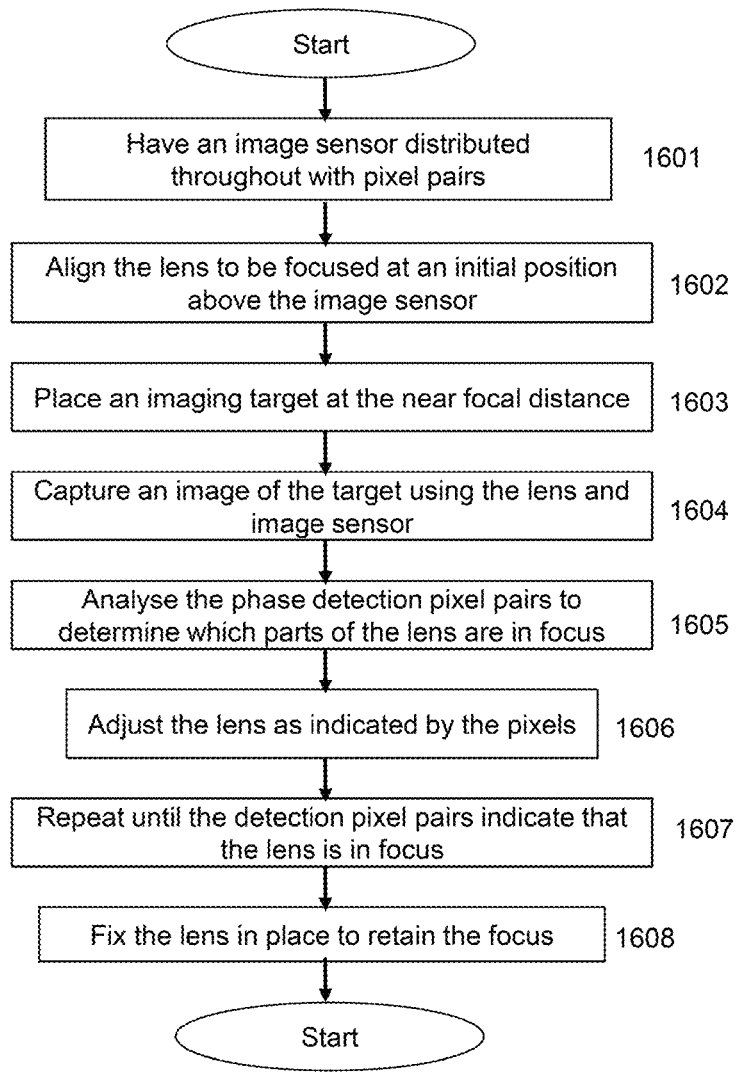
FIG. 16 is a flow chart illustrating an exemplary method of manufacturing an optical assembly using phase detection pixels, in accordance with some embodiments.

FIG. 16 is a flow chart illustrating an exemplary method of manufacturing an optical assembly using phase detection pixels, in accordance with one embodiment. At 1601, at least one pair of phase detection pixels is introduced in the manufacturing environment during the manufacturing of the optical assembly. In one embodiment, these pixel pairs are distributed throughout the sensor. The phase detection pixels are used to determine an optimum distance between the lens and the detector array, the distance enabling optimum focus for the lens assembly. In the next step, 1602, the lens is aligned to be focused at an initial position above the image sensor. Next, in 1603, an imaging target is placed at the near focal distance, that is, the object is placed at a known distance from the lens which is the presumed near focal point. An image of the target using the lens and image sensor is captured in step 1604. The responses of phase detection pixel pairs are measured. If the response of each pixel pair is equal or substantially equal within an accepted tolerance range, then the distance over which an object remains in focus is constant, or substantially constant within an accepted tolerance range, across the lens. If some of the pixel pairs responses are not equal, exceeding an accepted tolerance range, that means the distance over which an object remains in focus is varying and that may not be acceptable. This is shown in 1605. Thereafter, the lens is adjusted in the X, Y and/or Z axes, as indicated by the response of phase detection pixels distributed across the sensor, as shown in 1606. In one embodiment, the phase detection pixels represent less than 2%, and more than 0.01% of all pixels and are distributed throughout the pixel array such that each of four quadrants contains substantially the same number of phase detection pixels.

Steps 1604 through 1606 are repeated until the detection pixel pairs indicate that the lens is in focus in the X, Y and/or Z axes, as indicated in 1607. Optionally, in one embodiment, an imaging target may be placed at the far focal distance, or at multiple additional focal distances for a lens with focus capability. Thereafter, steps 1604 through 1606 may be repeated with additional focal distances until the detection pixel pairs indicate that the lens is in focus.

Finally, in step 1608 the optimum distance and angle determined between the lens and the detector array is fixed, to retain the focus, thereby enabling alignment of distance and tilt on the x and y axis.

Figure 17:
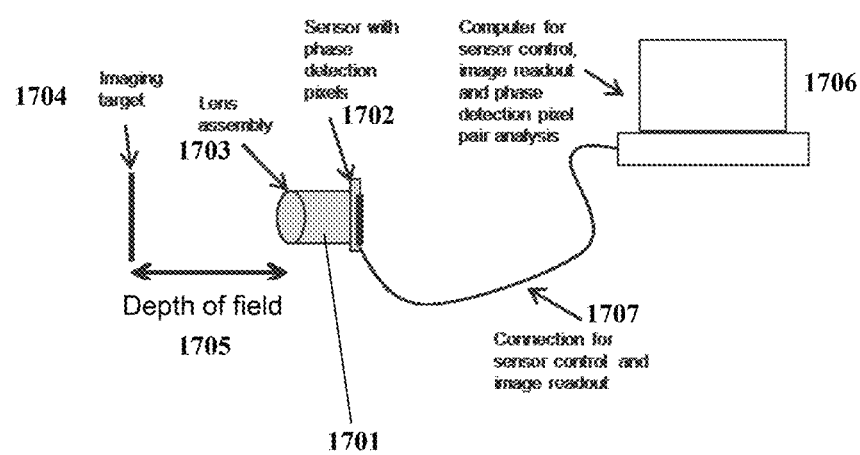
FIG. 17 illustrates an exemplary setup for ensuring the consistency of the depth of field across the entire lens, according to some embodiments.

FIG. 17 illustrates an exemplary setup for ensuring the consistency of the distance over which an object remains in focus across the entire lens. One of ordinary skill in the art would appreciate that this setup may be used during manufacturing an optical assembly, as well as for testing an optical assembly. Referring to FIG. 17, viewing element 1701 comprises a sensor 1702 that has several phase detection pixel pairs distributed across the detector array, and a lens assembly 1703. The pixel pairs are used to determine if an object is in focus at the desired focal length. Thus, an object (imaging target) 1704 is placed at a known distance 1705 from the lens, which is the presumed focal distance. The sensor 1702 is connected to a computer 1706 by means of a cable 1707. Computer 1706 controls the operation of sensor for image capture and also reads out the captured image. Further, as the computer reads out a captured image, it also analyzes the responses of pixel pairs. If all the pixel pair responses are equal, then the distance over which an object remains in focus is constant across the lens. If some of the pixel pair responses are not equal, it implies that the distance over which an object remains in focus is inconsistent. Based on the pixel response, the computer is able to isolate where the focus is different. In one embodiment, the computer displays a pixel map of phase detection pixel pairs to indicate which pixels are in focus and which are out of focus. Depending on these results, the lens may be adjusted to obtain a desired and consistent set of distances over which an object remains in focus.

In one embodiment, when the sensed image is visually processed by the computer, the phase detection pixel pair signals are removed or extrapolated out. This does not affect the image quality because phase detection pixels comprise a small fraction of the total number of pixels in the detector array.

Incorporating the phase detection pixels in the manufacturing environment has several advantages. As phase detection pixels result in alignment of a lens on the x, y, and z axis in a three-dimensional plane, it solves the problem of repeatedly and measurably achieving identical focus result across all axes (x, y, and z) in the manufacturing environment. The method of using phase detection pixels enables a repeatable manufacturing alignment process to achieve a consistent and optimal focus in the optical assembly. The present method is superior to other methods in that it allows for measurement points to be simultaneously taken throughout the field of view.

As mentioned above, the method and system of lens alignment as described in FIGS. 16 and 17, respectively, can be applied to a lens with a focus capability as well as a fixed focus lens. Further, the present method and system may be applied to any barrel design (threadless or threaded) used in the viewing elements.

In one embodiment, distance measurement techniques are used for dynamically projecting the estimated path of the scope beyond the distal tip during an endoscopic procedure. This provides guidance to the physician on the scope path, and also provides a measurement tool for the viewer to estimate distance and size of the objects of interest. Further, it improves efficiency of the procedure by potentially reducing the time necessary for scope insertion and also improves safety by reducing potential scope impacts on the wall of the colon.

Figure 18:
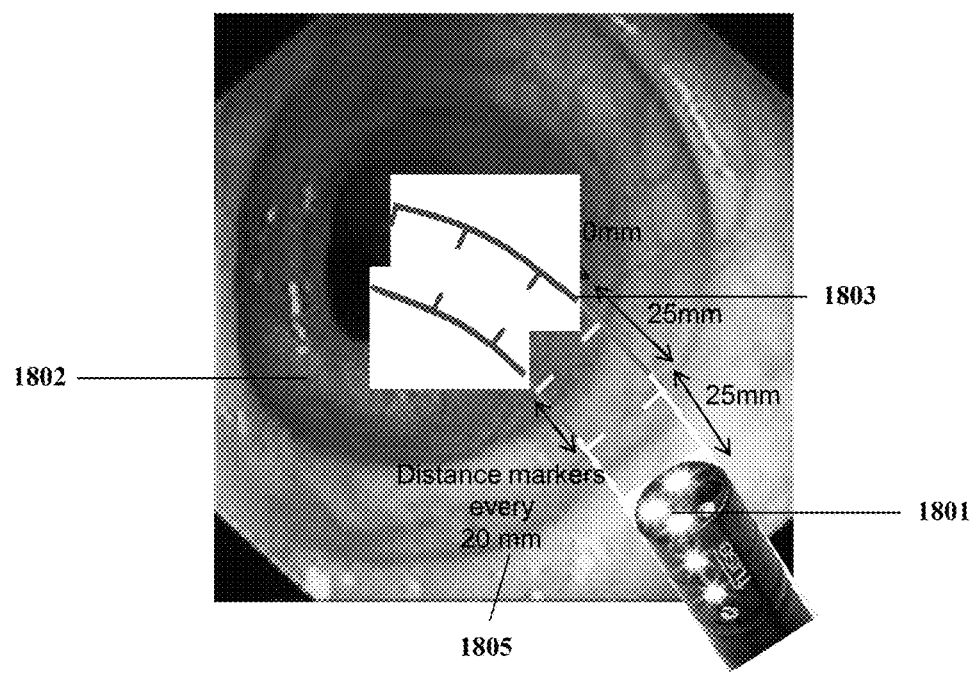
FIG. 18 is an exemplary screenshot illustrating graphical overlay of projected path on the endoscopic image, according to one embodiment.

FIG. 18 shows an exemplary screenshot illustrating graphical overlay of projected path on the endoscopic image. Referring to FIG. 18, distal tip 1801 of the endoscope moves through the lumen 1802 during an endoscopic procedure. Estimated path 1803 is dynamically computed and displayed over the image. In one embodiment, the total distance of the estimated path shown is equal to the furthest focus of the lens system of the front viewing element.

In one embodiment, the estimated path 1803 is color-coded, such that different colors are used for different levels of certainty of the projected path. One of ordinary skill in the art would appreciate that certainty of the projected path decreases with distance. Thus, for example, for total estimated path of 100 mm, the first 25 mm, which represents most certain path, may be shown in green. Thereafter, next 25 mm may be shown in yellow, while the last 50 mm, which represents the least certain portion of the estimated path, may be shown in red. Accordingly, each part of the path is color coded based on the degree of the certainty of the projected path, wherein a first part of the path has the highest degree of certainty and is of a first color, a subsequent, serially positioned second part of the path has the second highest degree of certainty and is of a second color, and a subsequent, serially positioned third part of the path has the third highest degree of certainty and is of a third color. The highest degree of certainty differs, on average, from the second degree of certainty and the third degree of certainty by predefined amounts. The second degree of certainty and the third degree of certainty also differ, on average, by predefined amounts.

In one embodiment, the projection includes marks or pointers 1805 at measured distances along the projected path, such as at every 20 mm. In one embodiment, distance markers 1805 are computed by calculating the distance to the walls of the colon, using distance measurement techniques as explained above.

One of ordinary skill in the art would appreciate that the endoscope is a flexible tube that is effectively rigid when pushed along a single axis. Inside the colon, an endoscope follows the path of the organ when straight but must be articulated to pass through the bends and corners in the lumen. This articulation is controlled by knobs on the endoscope handle, as shown in FIG. 1. In one embodiment, the articulation angle (left/right and up/down) is used to calculate the path the scope will follow in three dimensions, with the path approximating the articulation angle. In one embodiment, this estimate is further refined with distance information from pixels pairs, which provide a depth dimension. Further, the images captured from the viewing elements are used to provide the context of the scene.

Figure 19:
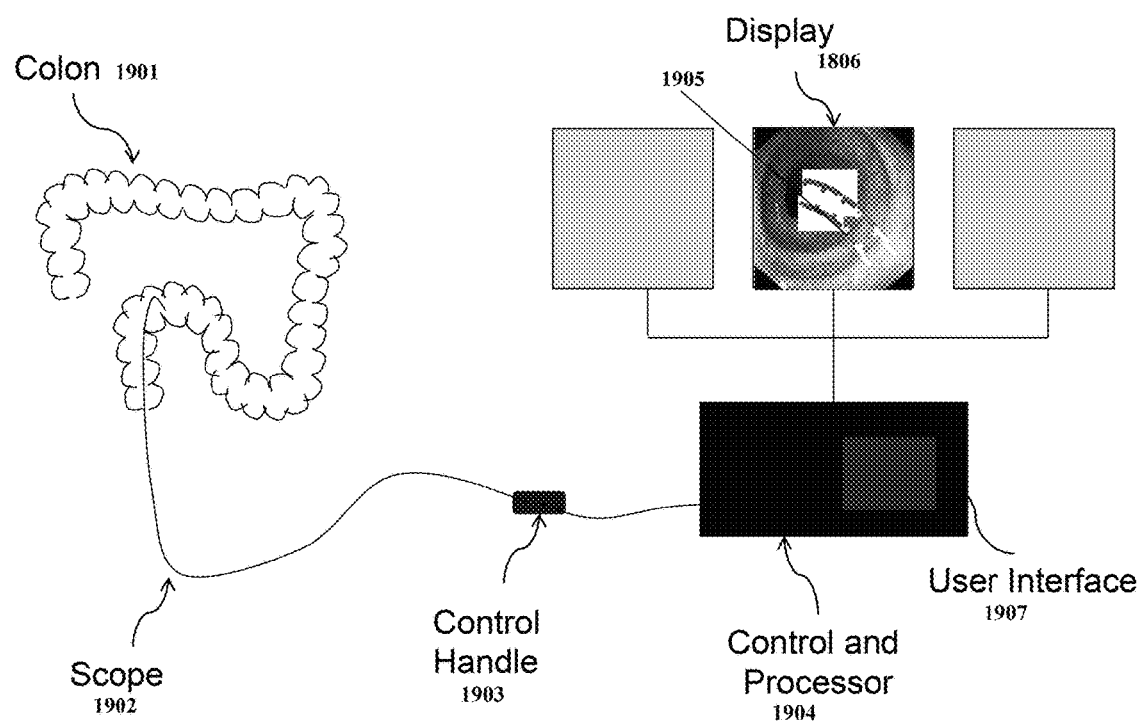
FIG. 19 illustrates the system for generation of graphic overlay showing the projected path, according to one embodiment.

FIG. 19 illustrates the basic system for generation of graphic overlay showing the projected path of the distal tip during an endoscopic procedure. During the procedure, an endoscope 1902 is maneuvered through the colon 1901 using the control handle 1903. The handle 1903 of the endoscope contains knobs and other control apparatus (as shown in FIG. 1) which are used by the operator to maneuver the endoscope. The rotation of knobs control the up/down and left/right angulation of the tip of the scope, and there is a direct correlation between control knob rotation and the angle of movement of the distal tip. The angulation data is sent to the controller/processor 1904 as input for the calculations on the estimated path of the scope and the generation of the overlays. The controller computes the estimated path of the scope based on a plurality of parameters which may include, incrementally or conditionally, the angulation data from the control knobs, distance measurements of the pixels and real-time images from the viewing elements on the scope. Based on the above information, the controller generates projection overlays for the estimated path. The projection 1905, which is a graphic overlay on the real-time video being captured by the endoscope, is thus calculated and inserted into the video and sent for display on the screen 1906. In one embodiment, the graphic is displayed in "2.5D" which includes perspective. "2.5D" is a term used to describe 2D graphical projections that produce a series of images to simulate the appearance of a 3D image.

As also described earlier, the controller 1904 is coupled to a user interface 1907. In one embodiment, the user interface of the endoscope system allows the operator to turn on or off the overlay function. Thus, for example, the overlay function may be turned on for a training mode or insertion, and turned off as desired during the procedure.

Figure 20:
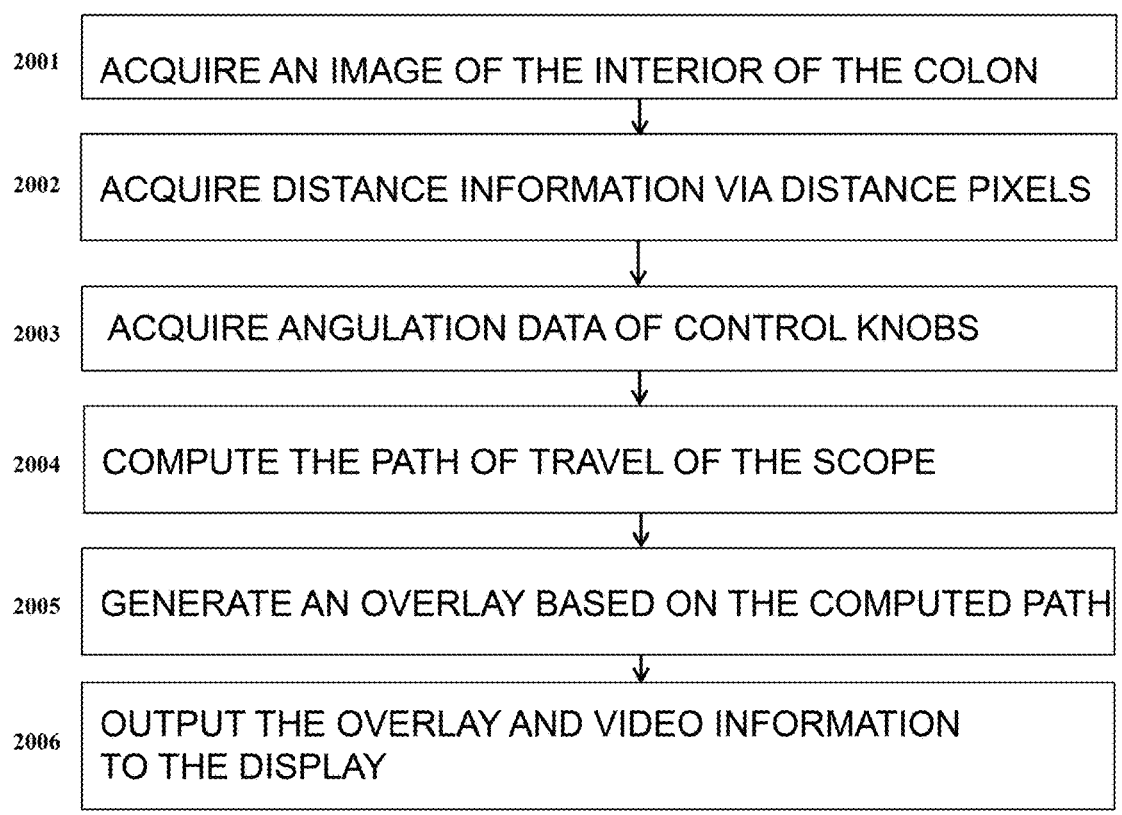
FIG. 20 is a flowchart illustrating the method for the calculation of the projected path and generation of the graphic overlay, according to one embodiment of the present specification.

FIG. 20 is a flowchart illustrating the method for the calculation of the projected path and generation of the graphic overlay. Referring to FIG. 20, an image of the interior of the colon is acquired by the controller during an endoscopic procedure in step 2001. Next, in step 2002, distance information is acquired using pixels pairs, as explained in previous embodiments. Thereafter, angulation data of control knobs is acquired, as shown in 2003. Based on the acquired information, an estimated path of movement for the scope is computed using an appropriate algorithm, as shown in 2004. Based on the estimated path an overlay is generated in 2005 and the overlay and video information is output to the display in step 2006.

Figure 21:
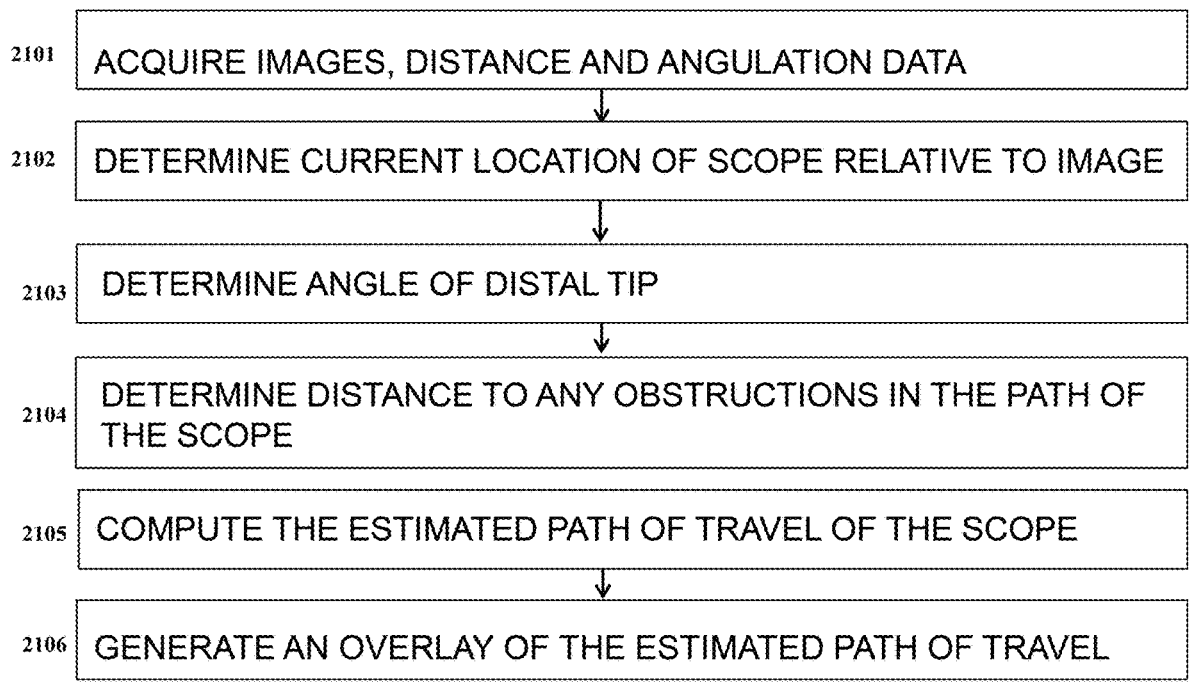
FIG. 21 is a flowchart illustrating an exemplary algorithm for computing an estimated path of movement of the endoscope during a procedure, according to one embodiment of the present specification.

FIG. 21 is a flowchart illustrating an exemplary algorithm for computing an estimated path of movement of the endoscope during a procedure. Referring to FIG. 21, firstly in step 2101 images, distance and angulation data are acquired, as explained above. Thereafter, the current location of scope relative to image is determined, in step 2102. Next, the angle of the distal tip is determined in step 2103. Thereafter in 2104, the controller determines the distance to any obstructions in the path of the scope. From the current location and angle of the tip, and the distance to obstructions (if any), an estimated path of travel of the scope is computed, as shown in step 2105. Finally, an overlay of the estimated path of travel is generated, as shown in step 2106.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for estimating a path of a distal tip of an endoscope during an endoscopic procedure, wherein the distal tip comprises a first viewing element, the method comprising:
    acquiring an image of an interior portion of a patient's body using the first viewing element;
    acquiring distance information of a distance to an object;
    acquiring angulation information of an angle to the object;
    calculating an estimated path of travel of the endoscope using the distance information and the angulation information;
    generating a graphical overlay using the estimated path of travel of the endoscope; and displaying the graphical overlay directly on a real-time image of an interior portion of the patient's body, wherein the real-time image is generated from at least the first viewing element;

wherein the graphical overlay is a projected path of travel of the distal tip; and wherein portions of the projected path of travel are displayed differently based on a degree of certainty of the respective portion of the projected path.

2. The method of claim 1, wherein the object is a surface of the interior portion of the patient's body, and acquiring distance information includes:

receiving light into a pair of photodiodes, wherein said light is reflected off of the surface of the interior portion of the patient's body;

determining a first response curve to said light for a first photodiode of the pair of photodiodes and a second response curve to the light for a second photodiode of the pair of photodiodes;

identifying an intersection between the first response curve and the second response curve; and using data derived from the intersection to determine the distance to the surface.

3. The method of claim 1, wherein a total distance of the projected path of travel is equal to the maximum focal distance of the first viewing element.

4. The method of claim 1, wherein the projected path of travel of the distal tip is a color-coded projected path of travel of the distal tip, wherein the projected path of travel is displayed in at least two colors, wherein a first color of the at least two colors represents a first degree of certainty of the projected path, and wherein a second color of the at least two colors represents a second degree of certainty of the projected path.

5. The method of claim 1, wherein the projected path of travel of the distal tip includes plurality of marks at measured distances along the projected path.

6. The method of claim 1, wherein acquiring information of the angle includes acquiring information of the angle using at least one control knob of the endoscope configured to control an articulation angle of the distal tip.

7. The method of claim 1, wherein the graphical overlay is displayed as a series of two-dimensional images configured to simulate the appearance of a three-dimensional image.

8. The method of claim 1, further comprising initiating the display of the graphical overlay via one or more actuators of a controller.

9. A method for estimating a path of a distal tip of an endoscope during an endoscopic procedure, wherein the distal tip comprises a first viewing element, the method comprising:

acquiring a first image of an interior portion of a patient's body using the first viewing element;

determining location information including a location of the distal tip relative to the first image;

determining distance information including a distance to an object within the image;

determining angle information including an angle of the distal tip using angulation information from at least one control knob of the endoscope;

calculating an estimated path of travel of the endoscope using the location information, the distance information, and the angle information;

generating a graphical overlay using the estimated path of travel of the endoscope; and displaying the graphical overlay;

wherein the graphical overlay is a color-coded projected path of travel of the distal tip, wherein the projected path of travel is displayed in at least two colors, wherein a first color of the at least two colors represents a first degree of certainty of the projected path, and wherein a second color of the at least two colors represents a second degree of certainty of the projected path.

10. The method of claim 9, wherein displaying the graphical overlay includes displaying the graphical overlay directly on a second image of an interior portion of the patient's body, wherein the second image is generated from at least the first viewing element.

11. The method of claim 9, wherein determining distance information includes:

receiving light into a pair of photodiodes of the first viewing element, wherein said light is reflected off of a surface of the interior portion of the patient's body;

determining a first response curve to said light for a first photodiode of the pair of photodiodes and a second response curve to the light for a second photodiode of the pair of photodiodes;

identifying an intersection between the first response curve and the second response curve; and using data derived from the intersection to determine the distance to the object.

12. The method of claim 9, wherein the graphical overlay is displayed as a series of two-dimensional images configured to simulate the appearance of a three-dimensional image.

13. A method for estimating a path of a distal tip of an endoscope during an endoscopic procedure, wherein the distal tip comprises a first viewing element, the method comprising:

acquiring a first image of an interior portion of a patient's body using the first viewing element;

determining location information including a location of the distal tip relative to the first image;

determining distance information including a distance to an object within the image;

determining angle information including an angle of the distal tip using angulation information from at least one actuator of the endoscope;

calculating a scale relative to the first image using the location information, the distance information, and the angle information;

generating a graphical overlay using the scale;

wherein the graphical overlay is displayed as a series of two-dimensional images configured to simulate the appearance of a three-dimensional image.

14. The method of claim 13, wherein the graphical overlay is a projected path of travel of the distal tip including a plurality of marks at measured distances along the projected path.

15. The method of claim 13, wherein determining distance information includes:

receiving light into a pair of photodiodes of the first viewing element, wherein said light is reflected off of a surface of the interior portion of the patient's body;

determining a first response curve to said light for a first photodiode of the pair of photodiodes and a second response curve to the light for a second photodiode of the pair of photodiodes;

identifying an intersection between the first response curve and the second response curve; and using data derived from the intersection to determine the distance to the object.

16. The method of claim 13, wherein the graphical overlay is a color-coded projected path of travel of the distal tip, wherein the projected path of travel is displayed in at least two colors, wherein a first color of the at least two colors represents a first degree of certainty of the projected path, and wherein a second color of the at least two colors represents a second degree of certainty of the projected path.

* * * * *